United States Patent
Wang et al.

(10) Patent No.: US 7,929,133 B2
(45) Date of Patent: *Apr. 19, 2011

(54) NANO STRUCTURED SENSING DEVICE FOR SURFACE-ENHANCED RAMAN SCATTERING

(75) Inventors: Hong Wang, Cupertino, CA (US); Xindi Wu, San Jose, CA (US); Xun Guo, Sacramento, CA (US)

(73) Assignee: Opto Trace Technologies, Inc., Mountain View, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 12/502,903

(22) Filed: Jul. 14, 2009

(65) Prior Publication Data

US 2010/0110424 A1    May 6, 2010

Related U.S. Application Data

(63) Continuation of application No. 12/262,667, filed on Oct. 31, 2008, now Pat. No. 7,576,854.

(51) Int. Cl.
*G01J 3/44* (2006.01)
*G01N 21/65* (2006.01)

(52) U.S. Cl. ........................................... 356/301
(58) Field of Classification Search .............. 356/301
See application file for complete search history.

(56) References Cited

U.S. PATENT DOCUMENTS

| | | | |
|---|---|---|---|
| 7,460,224 B2 * | 12/2008 | Wang et al. | 356/301 |
| 2006/0055922 A1 | 3/2006 | Li | |
| 2006/0164634 A1 | 7/2006 | Kamins | |
| 2006/0209300 A1 | 9/2006 | Kamins | |
| 2007/0177139 A1 | 8/2007 | Kamins | |
| 2007/0252979 A1 | 11/2007 | Bratkovski | |

* cited by examiner

*Primary Examiner* — F. L Evans
(74) *Attorney, Agent, or Firm* — Xin Wen

(57) ABSTRACT

A sensing device for surface-enhanced Raman spectroscopy (SERS) includes a substrate, a plurality of nano structures over the substrate, wherein at least one of the nano structures comprises an active SERS nano surface and an adsorption layer on the active SERS nano surface.

37 Claims, 27 Drawing Sheets

910

915

920

925

NANO STRUCTURED SENSING DEVICE FOR SURFACE-ENHANCED RAMAN SCATTERING

CROSS-REFERENCE TO RELATED APPLICATION

The present application is a continuation of and claims priority to commonly assigned U.S. patent application Ser. No. 12/262,667, filed Oct. 31, 2008 now U.S. Pat. No. 7,576, 854, titled "Arrays of nano structures for surface-enhanced Raman scattering", which claims priority to U.S. patent application Ser. No. 11/562,409 (issued now as U.S. Pat. No. 7,460,224), filed Nov. 21, 2006. U.S. patent application Ser. No. 11/562,409 further claims priority to U.S. Provisional Patent Application 60/751,472, filed on Dec. 19, 2005. The disclosure in these related patent applications are incorporated herein by reference.

FIELD OF INVENTION

This invention relates to trace chemical detection using surface light scattering techniques.

BACKGROUND OF INVENTION

Raman scattering was discovered in 1928 and named after the scientist C.V. Raman, who received the 1930 Nobel Prize in Physics because of this discovery.

Raman scattering is an inelastic scattering of a photon which creates or annihilates an optical phonon. Raman scattering is the result of the interaction of incident photons with chemical molecular vibrations (phonons). A unique chemical molecular structure results in a unique Raman scattering spectrum. Therefore, Raman scattering provides spectral fingerprint details about the chemicals, and can also be used to distinguish molecular isomers or even chiral molecules from each other.

Raman spectroscopy was commercially available after invention of lasers in late 1960. A laser beam having a narrow line width is used to illuminate the testing chemicals in solid, liquid or gas forms. The narrow line width of the laser beam can eliminate the overlaps of scattering peaks from photons (lights) with various wavelengths. The scattered light is collected by a photon detector such as Charge-Coupled Devices (CCD) or CMOS detector, a Raman spectrum is collected. The Raman shift is defined as the wavelength spacing between the scattering light wavelength and incident light wavelength (laser wavelength). The positions of the peaks correspond to the vibration strengths of various molecular bonds, thus provide a spectral fingerprint of the molecules.

Although Raman scattering is a useful analytical tool, it suffers a major drawback: the scattering signal is very weak due to the very small scattering cross section of molecules. Typically, only about $10^{-8}$ of the incident photons on the chemicals will undergo Raman scattering. Of course, high power laser and high sensitivity CCD detector can be used to improve the scattering signals but coming with the extra costs, additional hardware, and unexpected sample damage. Because of the weak scattering signals, normal Raman scattering application is relatively broad but still very limited.

Surface-enhancement effect by using a roughened surface was found to boost Raman scattering signal. In Surface-Enhanced Raman Spectroscopy (SERS), the sample surface can be formed by deposition of metallic particles or clusters. The surface-enhanced Raman scattering phenomena can be explained by interaction between photons with localized electromagnetic field enhancement and chemical enhancement. The enhancement by SERS has been observed in different research labs. An Intel team used a porous silicon structure with coatings of noble metals such as silver on the surface. The Intel team demonstrated that the enhancement increases as the porous silicon pore-size decreases. All the experiments including the work from Intel can be repeated by another team, but it is difficult to reproducibly demonstrate the same level of enhancement.

Accordingly, there is a need to develop well-controlled nano-surface structures at low cost in order to realize commercialization of SERS for various applications ranging from cargo inspection, food inspection, environment monitoring, disease diagnosis, to forensic and homeland security. There is a need to improve the performance of SERS devices and processing techniques for making the same.

SUMMARY OF THE INVENTION

The present invention provides a novel surface device comprising a substrate supporting a plurality of nano structures and an exposed sensing surface upon the nano structures, wherein said surface includes at least one active SERS nano surface and at least one inactive SERS nano surface established in proximity to the active SERS nano surface.

An objective of the invention is to provide functions in the array of the nano-structures to enhance the chemical adsorption to the array surfaces, thus further improve the SERS sensitivity. In one embodiment, the charge states of the measured chemicals are utilized. Electrical bias can be applied to the nano-structures or to a function layer built under the nano-structure surface to attract the chemicals to the array surface. The bias can be varied from negative to positive based on chemical properties of the measured chemicals by SERS. In another embodiment, a thin chemical function layer with special surface bonds to attract the measured chemicals is constructed. In another embodiment, cooling the whole array structure with the substrate to a specific temperature is designed to selectively condense the measured chemicals to the array surface. In another embodiment, a magnetic filed is applied to the sensing surface, or function layer at the sensing surface containing magnetic materials, such as Fe, Co, Ni, or their compounds. In this way, the chemical polar molecules on the sensing surface, would have statistically aligned to a preferred orientation. The effect of applied magnetic field or active layer built-in localized magnetic materials is to enhance chemical specific binding, to enhance molecule surface binding efficiency, i.e., enhancing chemical molecule adsorption onto the sensing surface with maximized number of molecules within unit period of time, resulting enhanced Raman signal.

The present invention also provides a method of forming a surface sensing device comprising: providing a substrate, depositing at least one layer of material upon the substrate, establishing a pattern upon the layer of material, the pattern defining a plurality of nano structures, removing a portion of the layer of material to define side walls of the nano structure, and forming an exposed sensing surface upon the nano structures, wherein said surface includes at least one active SERS nano surface and at least one inactive SERS nano surface established in proximity to the active SERS nano surface.

One embodiment provides a novel method to make various shapes, such as square, rectangular, circle and so on, of arrays on a specific substrate or various substrates, create the arrays of nano-structures in the format of rods or holes. These nano-structures could be either isolated islands or connected one another.

In accordance with one aspect of the present invention, the nano structures are built on a substrate. Non-limiting examples of the substrate include silicon, GaAs, ZnS, CdSe, sapphire, $Al_2O_3$, glass, Ti, Ni, Cr, Al, and Cu.

Additional objects of the invention are attained by the selection of specific materials for the array of nano surface structure, surface functional layer or thermal bias layer. The material is selected from the group of noble metal and transition metal, including but not limited to Ag, Au, Cu, Al, Fe, Co, Ni, Ru, Rh, Pd, and Pt for nano structure substrate. The choice for the surface function layer includes but not limited to Ag oxide, Au oxide, $SiO_2$, $Al_2O_3$, $Si_3N_4$, $Ta_2O_5$, $TiO_2$, ZnO, $ZrO_2$, $HfO_2$, $Y_2O_3$, Tin oxide, antimony oxide, and other oxides; Ag doped with chlorine or chloride, Au doped chlorine or chloride, Ethylene and Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), Polyvinylprorolidone (PVP), and other polymers; stacked multiple layers at least two layers including above listed metal layers and non-metal layers, etc. The thermal bias layer can be electrically isolated or connected to the array. A typical material is a metal such as Ti, Ni, Cr, Pt, Ru, Ni—Cr alloy, NiCrN, Pt—Rh alloy, Cu—Au—Co alloy, Ir—Rh alloy or/and W—Re alloy.

Further object of the invention is to define the distributions, and dimensions for the array of nano surface structures, the surface function layer and bias layer. In one embodiment, the array has the dimension of each nano structure between 1 nm to 300 nm, preferably 5 nm to 50 nm, with a spacing of 1 nm to 1000 nm, preferably 5 nm to 50 nm between the structures. In accordance with one aspect of the present invention, the array of nano structure has a depth or height between 1 nm to 100 nm preferably 5 nm to 10 nm. The surface function layer thickness is between 0.5 nm-500 nm, or preferred between 2 nm-20 nm. The bias layer thickness is between 50 nm to 10 μm or preferred between 50 nm to 500 nm.

Still further objective of the invention is to define the geometry shapes of the array of nano surface structures. The shape of holes or rods of the nano structures have a geometry selected from at least one of circular, triangle, quasi-triangle, square, rectangular, hexagonal, oval, elliptical, rectangular with a semi-circles or tri-angles with rounded corner at both ends alone either long or short axis, and rectangular with four rounded corners.

In one aspect of the present invention, a trace chemical substance detection system is provided. The system comprises a spectroscopy system operatively associated with a surface device comprising: a substrate supporting a plurality of nano structures, an exposed sensing surface upon the nano structures, wherein said surface includes at least one active SERS nano surface and at least one inactive SERS nano surface established in proximity to the active SERS nano SERS surface. In one embodiment, the spectroscopy system comprises a laser beam source generating a laser beam, an optical assembly focusing the laser beam, an deflection system directing the laser beam at an array device, a collector receiving a portion of said laser beam scattered by said array device; and an spectrum analyzer receiving said portion and generating an output indicative of the composition and or concentration of chemicals on the array device.

One objective of the present invention is to use the array of nano surface structure for SERS applications for liquid and gas phase measurements of trace chemical detections. It can be also applied the array to other spectroscopy measurements including surface-enhanced Raman resonance spectroscopy (SERRS), surface-enhanced coherent-anti stokes Raman scattering (SECARS), surface-enhanced infrared absorption (SEIRA) spectroscopy, surface-enhanced fluorescence spectroscopy, surface-enhanced photoluminescence spectroscopy, time-resolved measurements with above techniques, and combination of above techniques for chemical fingerprint identification and trace chemical sensing.

Yet another objective of the invention is to provide an in-situ cleaning method for the array. Thermal-electrical heating is applied to the bias metallic layer to heat array of the nano surface structure up to 500° C. Many adsorbed chemical molecules and unexpected surface contamination will be physically evaporated or even burn out at the high temperature, resulting in a clean array to prevent cross contamination of previous measurements, and reuse of the array for SERS.

Yet another embodiment in accordance with the present invention provides a method of detecting molecules comprising: a) introducing a trace amount of chemical onto an array device allowing molecules of the chemical being adsorbed onto an sensing surface of the array device, b) irradiating the array device with a laser beam, c) collecting scattered photons from the adsorbed molecules, and d) detecting Raman spectrum from the scattered photons; wherein said array device comprises a substrate supporting a plurality of nano structures, the exposed sensing surface upon the nano structures, wherein said surface includes at least one active SERS nano surface and at least one inactive SERS nano surface established in proximity to the active SERS nano surface.

With above mentioned points, one is able to effectively enhance chemical specific binding, to enhance molecule surface binding efficiency, i.e., to enhance chemical molecule adsorption onto the sensing surface with maximized number of molecules within unit period of time, so that to enhance Raman signal.

DETAILED DESCRIPTION OF THE INVENTION

Figure 1:
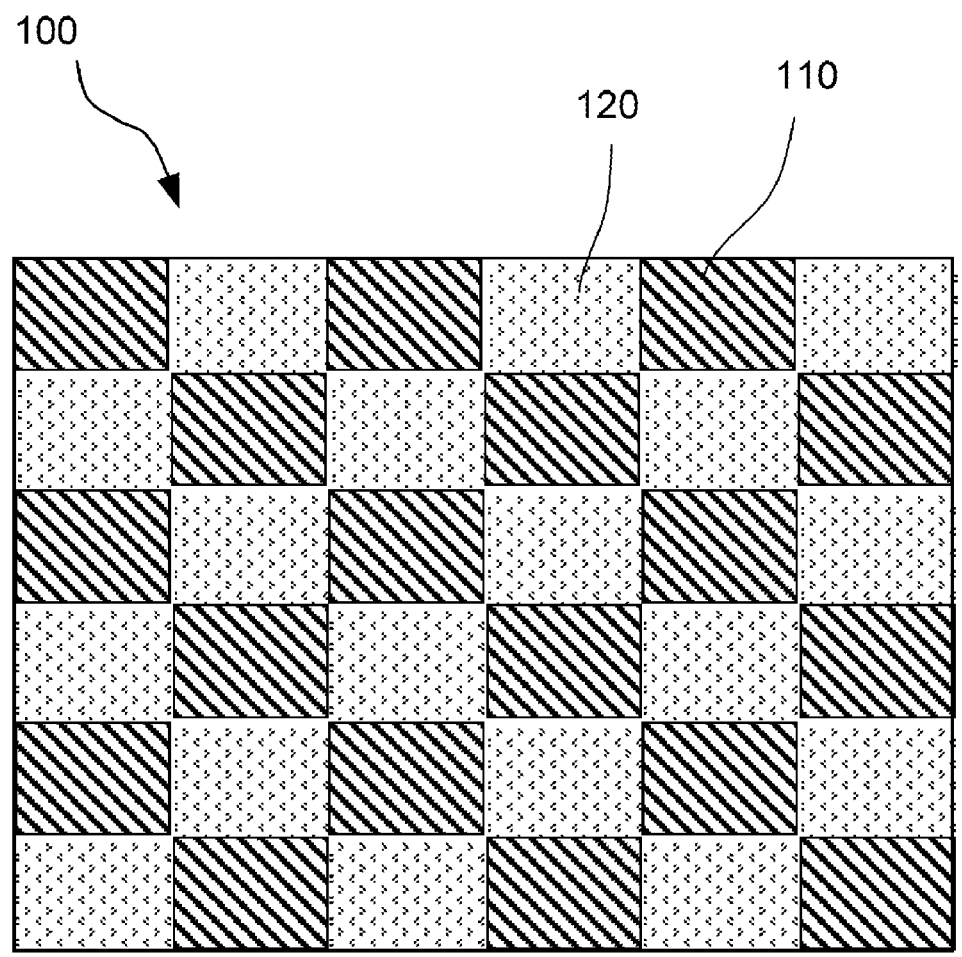
FIG. 1 is a top view of a square array of an array device according to one embodiment of the present invention.

The present invention provides new devices and apparatus/systems as well as methods for improved performance of Surface-Enhanced Raman spectroscopy.

SERS selectivity of surface signal results from the presence of surface enhancement mechanisms demonstrated only at the surface. There are two primary mechanisms of surface enhancement: electromagnetic enhancement and chemical enhancement. The electromagnetic enhancement is dependent on rough features present on the metal surface, while the chemical enhancement involves electronic charge transfer and changes to the adsorbate electronic states due to chemisorption of the analytes.

SERS is observed primarily from analytes adsorbed onto coinage (Au, Ag, Cu) or alkali (Li, Na, K) metal surfaces, with the excitation wavelength near or in the visible region. Theoretically, any metal would be capable of exhibiting the effect of surface enhancement, but the coinage and alkali metals satisfy calculable requirements and provide the strongest enhancement.

The great part of the overall enhancement of SERS is due to an electromagnetic enhancement mechanism that is a direct consequence of the presence of metal roughness features on the metal surface.

The chemical enhancement mechanism also provides enhancement for the gain of Raman signal intensity. The molecule is adsorbed onto the surface and interacts with the surface. The chemical enhancement exists because of this interaction. The metal adsorbate proximity allows pathways of electronic coupling from which novel charge-transfer intermediates emerge, leading to a SERS condition with higher Raman scattering cross-sections. In addition, the electronic orbits of the adsorbate molecules may contact and interact with the conducting electrons of the metal, altering the chemical state of the chemical substance. It is also proposed that the chemical enhancement may be an alteration in the scattering cross-section, which is the chemical nature of the chemical substance changing due to its interaction with the metal.

The present invention provides an array device comprising a substrate supporting a plurality of nano structures and an exposed sensing surface upon the nano structures, wherein said surface includes at least one active SERS nano surface and at least one inactive SERS nano surface established in proximity to the active SERS nano surface. Accordingly, the performance of this SERS device benefits from both electromagnetic effect and chemical enhancement to the Raman signal intensity.

The term, "active SERS nano surface", when used herein, encompasses a well defined metal surface having at least one surface dimension on a nanometer scale. The surface may or may not be flat. The active SERS nano surface exhibits electromagnetic enhancement to Raman signal under photon irradiation. Examples of materials for the active SERS surface include noble metal such as Ag, Au, Cu, and Pt, and transition metals such as Al, Fe, Co, Ni, Ru, Rh, and Pd. The material used for the active SERS surface is referred as "active material".

The term, "inactive SERS nano surface", refers to a well defined surface having at lease one surface dimension on a nanometer scale. The surface may or may not be flat. In contrary to the active SERS nano surface, the inactive SERS nano surface does not exhibit significant electromagnetic enhancement to Raman signal just by itself. However, when the inactive SERS surface was placed in proximity to the active SERS nano surface, a relatively stronger enhancement of Raman signal was observed, compared with the signal from merely the active SERS nano surface. Therefore, the inactive SERS nano surface arranged in an alternative fashion with the active SERS surface provides further enhancement to Raman signal. Examples of materials for the inactive SERS nano surface include insulators such as $SiO_2$, $Al_2O_3$, $Si_3N_4$, $Ta_2O_5$, $TiO_2$, and air (open space). The material used for the inactive SERS nano surface is referred as "inactive material".

The term, "nano structure", as used herein, is intended to mean a 3-dimensional object either extruded away from the substrate or recessed toward the substrate, having at least one dimension on a nanometer scale. Non-limiting examples of the shape of the nano structure include nano rod, nano pyramid, nano hole, and nano pit.

According to one embodiment of the present invention, an improved SERS performance is achieved by arranging the inactive SERS nano surface next to the nano active SERS surface. FIGS. 1-11 provide exemplary array devices for improved SERS applications.

FIG. 1 shows a top view of a square array 100 with a plurality of active SERS nano surfaces 110 and inactive SERS nano surfaces 120 established on a substrate. As shown in FIG. 1, each active SERS nano surface is alternatively arranged with each inactive nano SERS surface. The active SERS surfaces are made from a material selected from a group of noble metals, including but not limited to Ag, Au, Cu and Pt. The active SERS surfaces may also be made from a material selected from a group of transition metals, including but not limited to Al, Fe, Co, Ni, Ru, Rh, and Pd. The inactive SERS nano surfaces are made from insulating materials, including but not limited to $SiO_2$, $Al_2O_3$, $Si_3N_4$, $Ta_2O_5$, $TiO_2$, and open space (air).

Figure 2A:
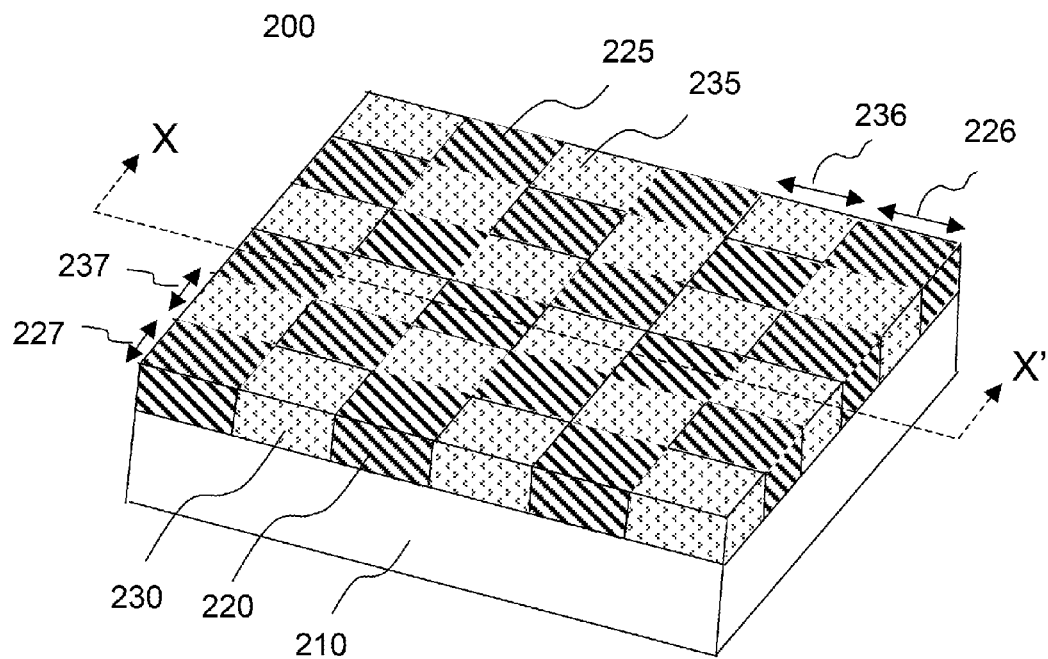
FIG. 2 shows a square array according to one embodiment of the present invention.

FIG. 2A shows a perspective view of an array device 200 according to one aspect of the present invention. The device comprises a substrate 210, an array of rectangular rods 220 made of an active material and an array of rectangular rods 230 made of an inactive material. Each active rod 220 is alternatively arranged with each inactive rod 230. The active rod 220 provides the active SERS nano surface 225 and the inactive rod 230 provides the inactive nano SERS 235. Both surfaces 225 and 235 are substantially square, having dimensions of 226, 227, 236, and 237 between about 5 nm to 300 nm. In one embodiment, the dimension of the squares is between about 1 nm and about 10 µm.

Figure 2B:
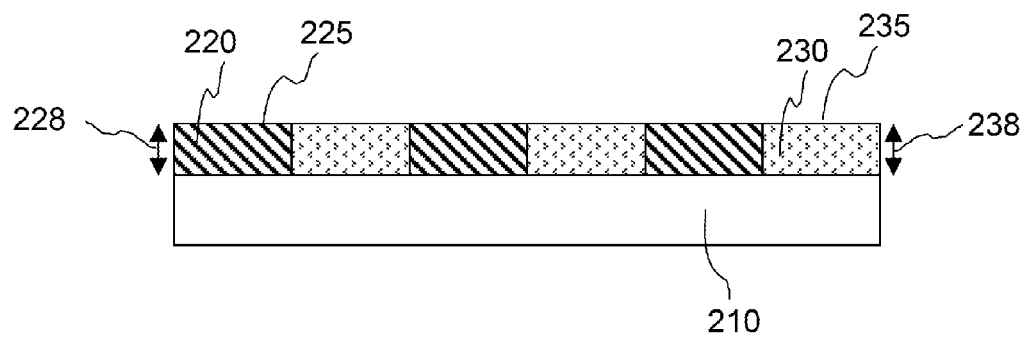

FIG. 2B is a sectional view of the structure of FIG. 2A, sliced at line X-X' of the structure shown in FIG. 1. The height 228 of the active surface 225 is substantially equal to the height 238 of the inactive surface 235. The height 228 and 238 is between 5 nm to 100 nm. In one embodiment, the height 228 and 238 is between 1 nm to 5 µm.

Figure 3A:
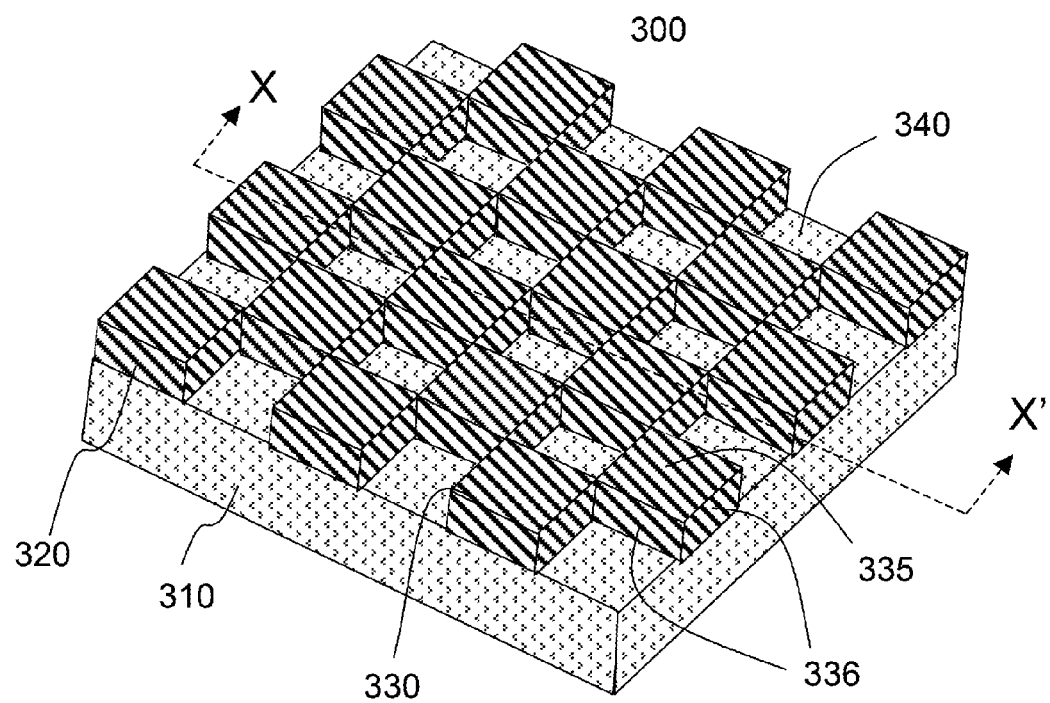
FIG. 3 shows a square array according to another embodiment of the present invention.
Figure 3B:
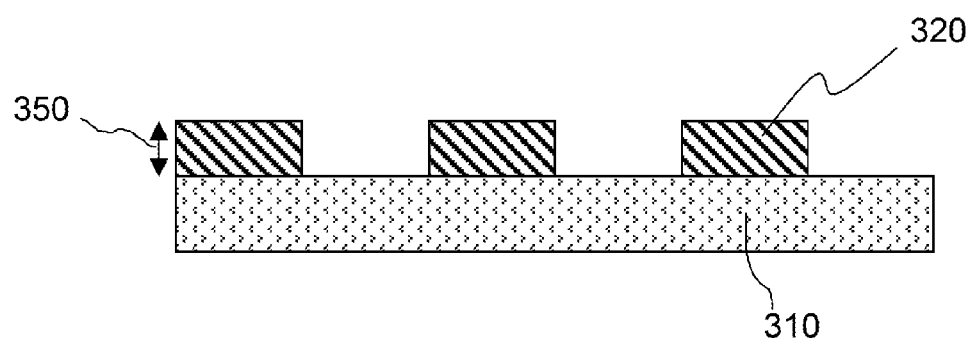

FIG. 3A shows a perspective view of another square array 300. The substrate 310 is made from an inactive material. A plurality of square rods 320 are disposed on the substrate. The rod 320 provides the active SERS nano surface 330, which includes top surface 335 and side wall 336. The active SERS nano surface 330 is surrounded by four square areas 340 of inactive SERS nano surfaces. The square area 335 of the active SERS surface is substantially equal to the inactive area 340. A sectional view of a cutoff at line X-X' is shown in FIG. 3B. The height 350 of the rod 320 is between 5 nm to 100 nm. In one embodiment, the height 350 of the rod 320 is between 1 nm to 5 µm.

It is to be understood that essentially the detection sensitivity of the Raman scattering sensors can be enhanced when at least a portion of the nano structures or nano surfaces (active or inactive) has a nano feature size functionally matched with a characteristic parameter of electrons or phonons such as an electron mean-free path (MFP) of electrons on the surface, electron wavelength of electrons on the surface, a phonon MFP of phonons on the surface and a phonon wavelength of phonons on the surface.

The term, "nano feature size", used herein is refereed to the diameter of an active nano SERS surface, the diameter of an inactive nano SERS surface, the height or depth of an nano rod or nano hole, or the spacing between nano structures in the array device.

The term, "functionally match" as described above may include the condition that the nano feature size is approximately equal to, smaller than, integer numbers of, or with a special mathematical function to the characteristic parameter of electrons or phonons.

Figure 4:
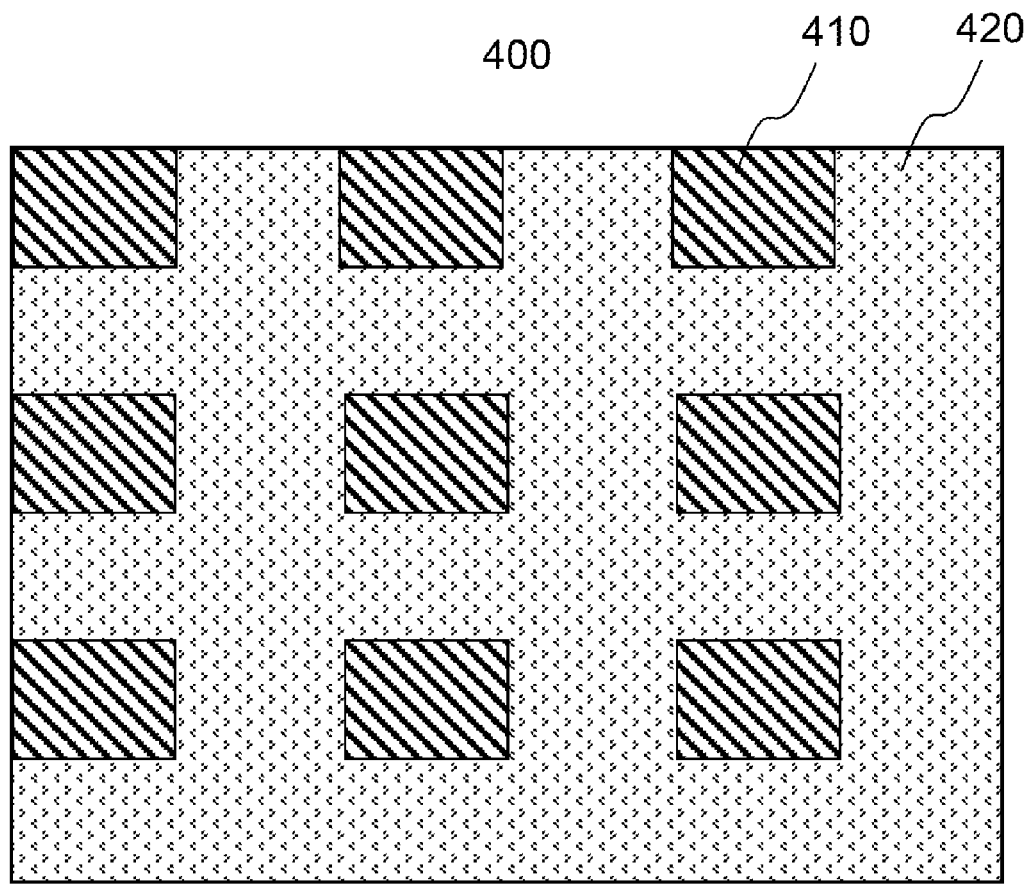
FIG. 4 is a top view of another square array according to one embodiment of the present invention.

FIG. 4 shows another example of a square array 400 of nano surface structure where the active SERS surfaces 410 are physically isolated from each other by inactive SERS nano surface 420. Again, the spacing between the active areas can be air or insulating materials as illustrated in FIGS. 2 and 3.

Figure 5A:
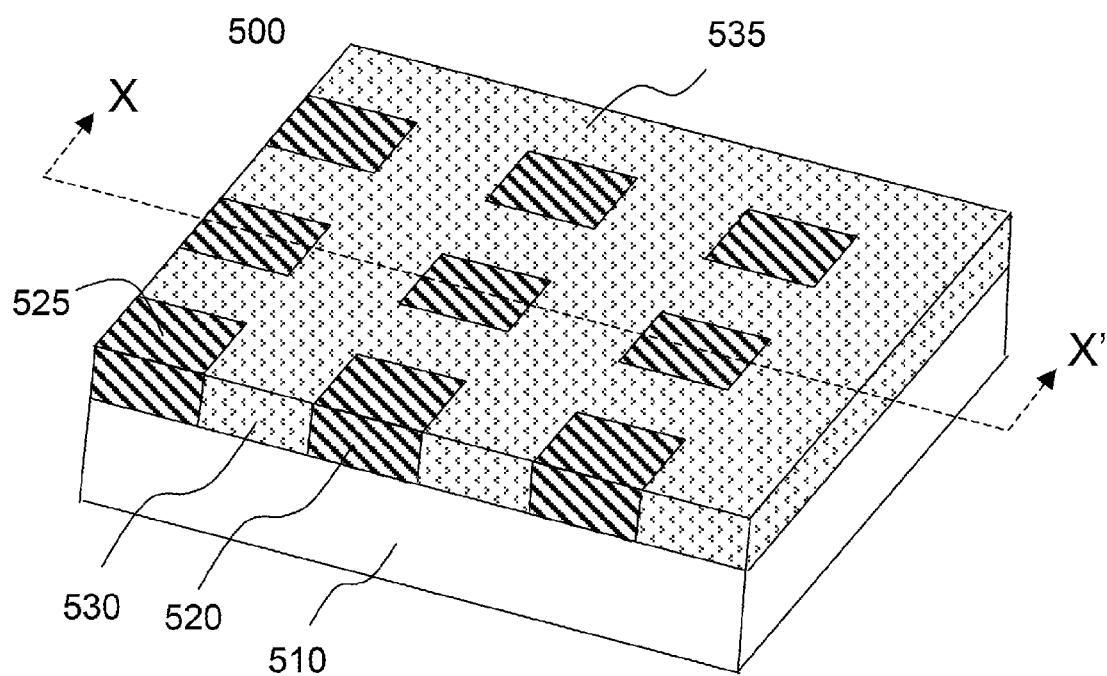
FIG. 5 shows a square array with isolated active areas and surrounding inactive areas.
Figure 5B:
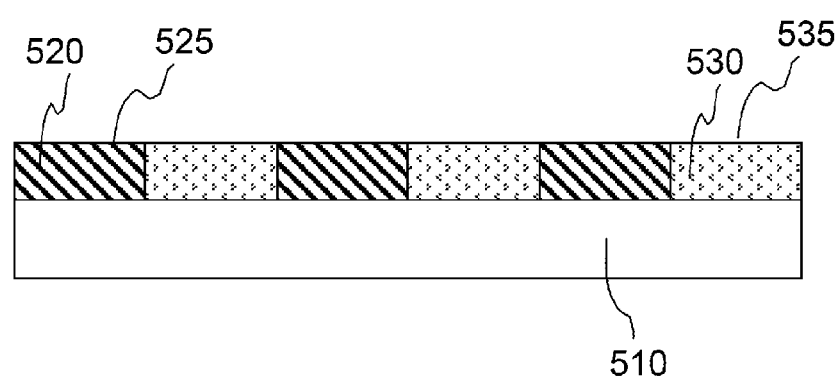

Referring now to FIGS. 5A and 5B, an array device 500 having square rods 520 of an active material is established on a substrate 510. Each rod 520 is surrounded by a region 530 made of an inactive material. A cutoff view from line X-X' is shown in FIG. 5B. Each active SERS nano surface 525 is isolated by an inactive nano surface 535.

Figure 6A:
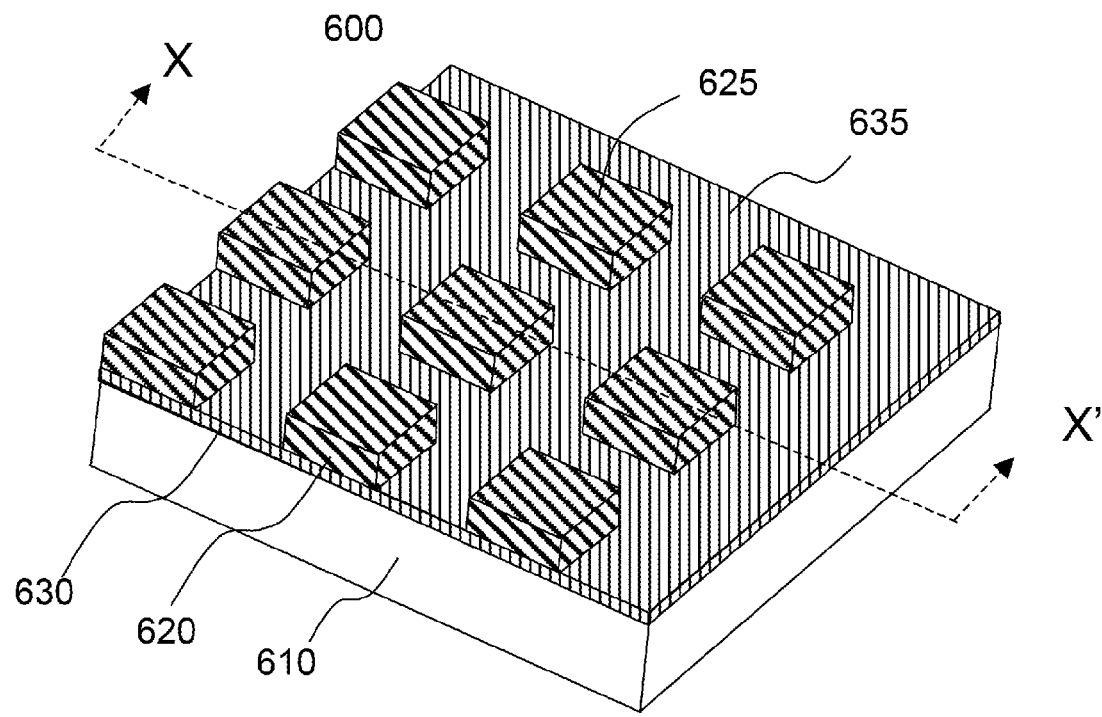
FIG. 6 shows a square array with a layer of active material connecting each of the active nano surface structure.
Figure 6B:
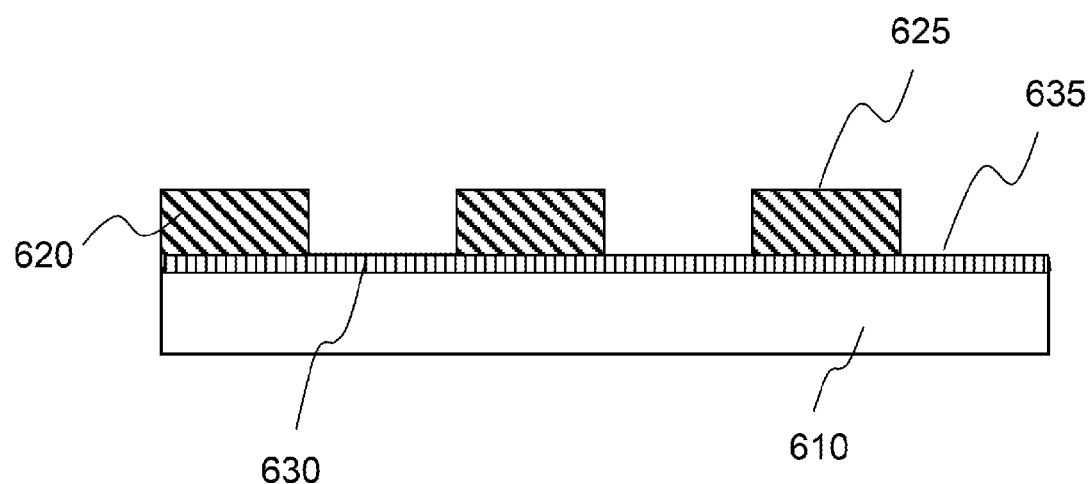

In some embodiments, FIG. 6A is a perspective view showing an array device 600 having a substrate 610 covered by a layer 630 of an active material. Square rods 620 of another active material established on the layer 630. A cutoff view from line X-X' is shown in FIG. 6B. Each active SERS nano surface 625 is isolated by another active nano surface 635. In a special case, a same active material is used for both square rods 620 and layer 630 and the active structures are connected at the bottom of the active areas. The connecting materials can be same as in the active area or different conductors.

It is to be understood that the shape of the nano structure may be altered as desired for a particular application. FIGS. 7 through 9C provide examples of various shapes of nano rods or nano holes.

Figure 7:
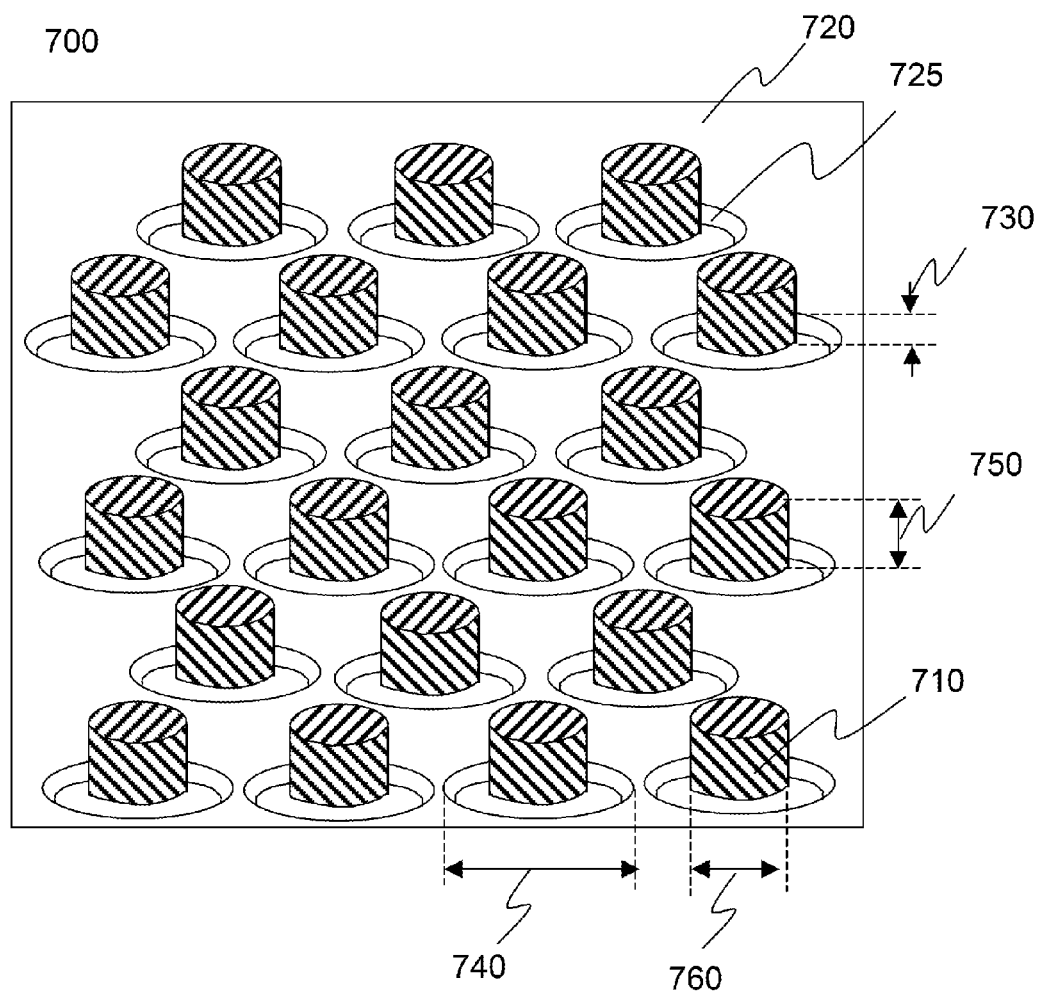
FIG. 7 is a three dimensional view of cylindrical form of array of independent active nano surface structures on surrounding inactive area, with an inactive area depression at the bottom of each of the active nano surface structures.

FIG. 7 shows a perspective view of cylindrical form of array of nano surface structures 700. The independent active areas in their cylindrical forms 710 are regularly distributed on surrounding inactive area 720 to form an array of the nano surface structures 700. The bottom of each of the active cylinder is situated on a depression 725 in the inactive area 720. The depth 730 of each of the depression in the inactive area is smaller than the height 750 of the cylindrical active rod 710. The diameter 740 of the depression 725 is larger than the diameter 760 of the active rod by a distance on a nanometer scale. Various geometrical features can be designated to maximize the adsorption of molecules. The depression shown on this figure is one of the examples of the enhancement providing structure.

Figure 8A:
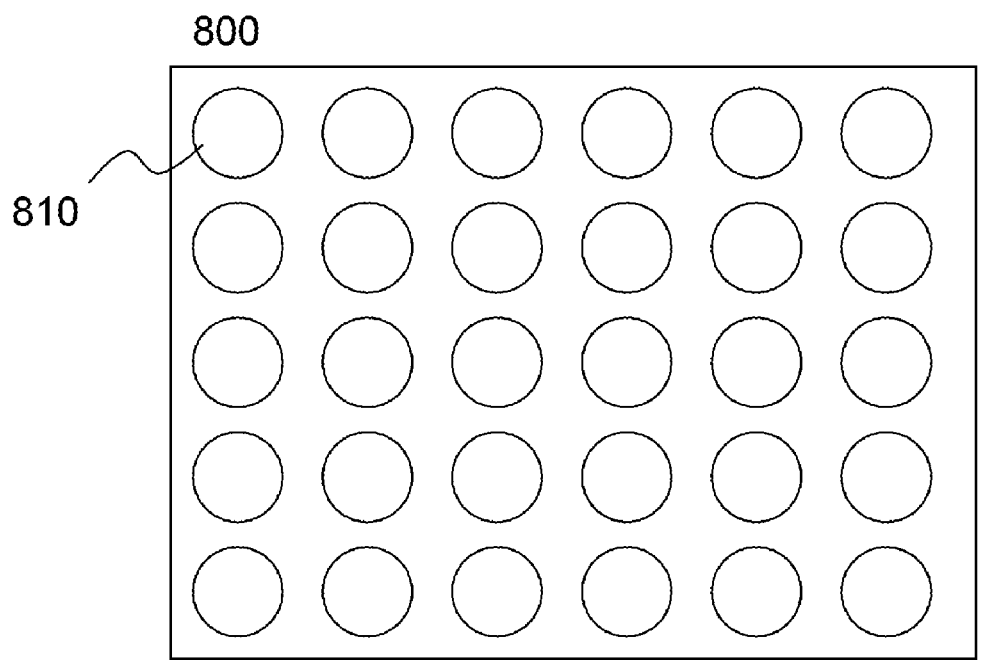
FIG. 8 is a top view of a circular array.
Figure 8B:
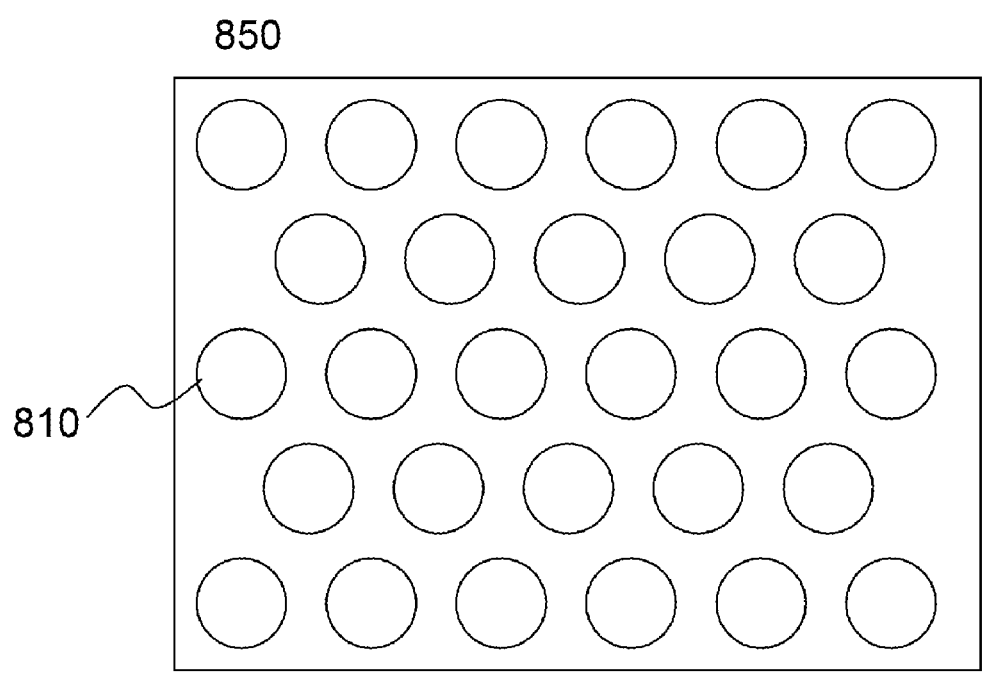

FIG. 8A shows a top view of circular array 800 of nano surface structures which are regularly distributed on a substrate. The area in circles 810 can be the active SERS nano surface or the inactive SERS nano surface (or even air, meaning empty). FIG. 8B shows a top view of another circular array 850 of nano surface structure with a tight packaging of the circles on a substrate.

Figure 9A:
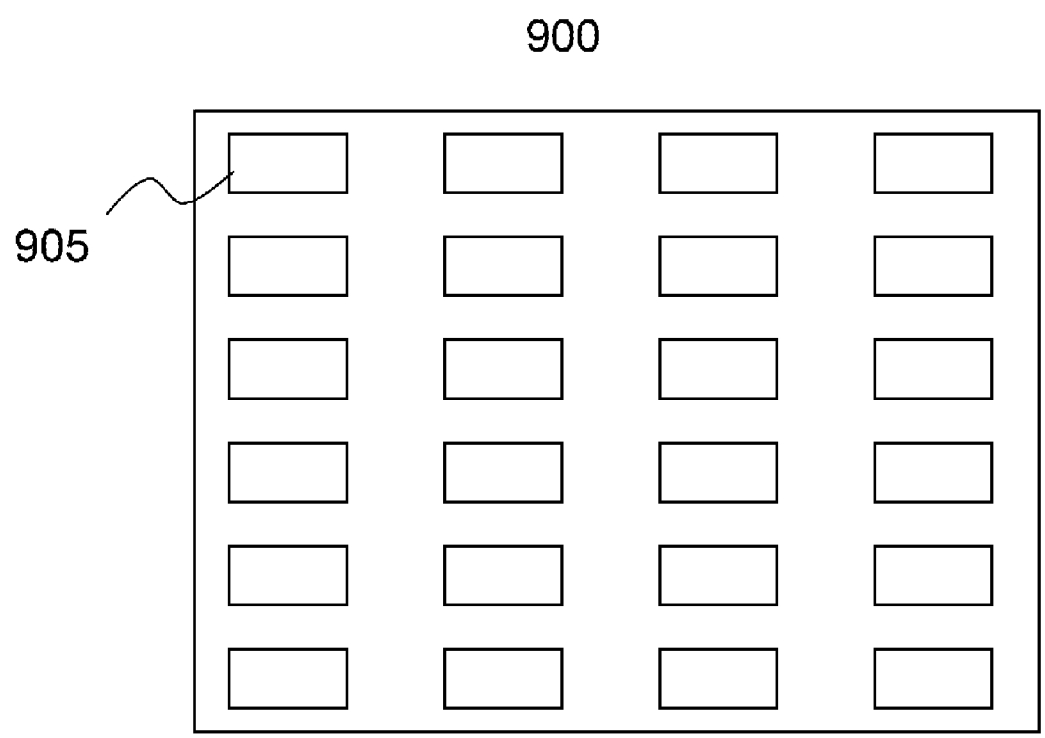
FIG. 9 shows top views of arrays of various shapes.
Figure 9B:
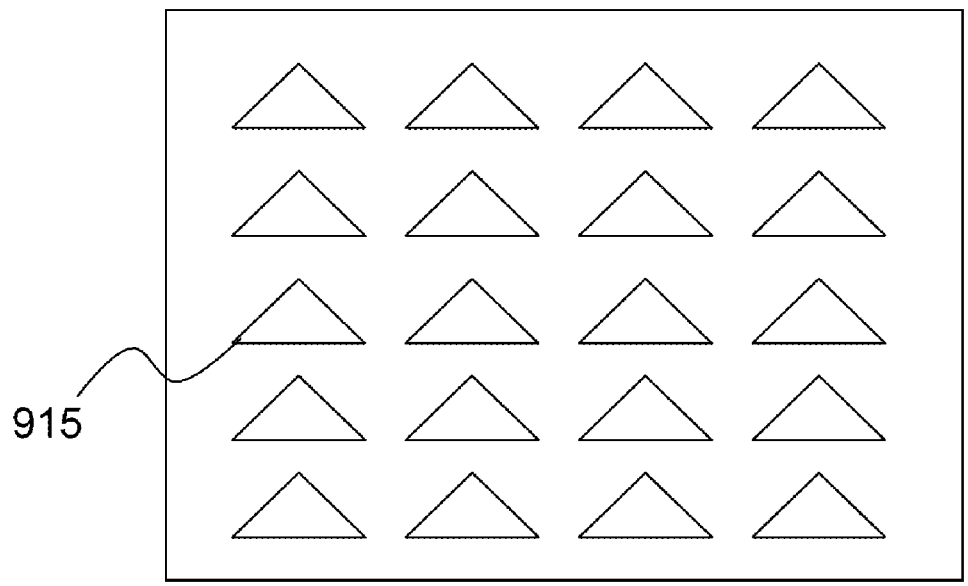
Figure 9C:
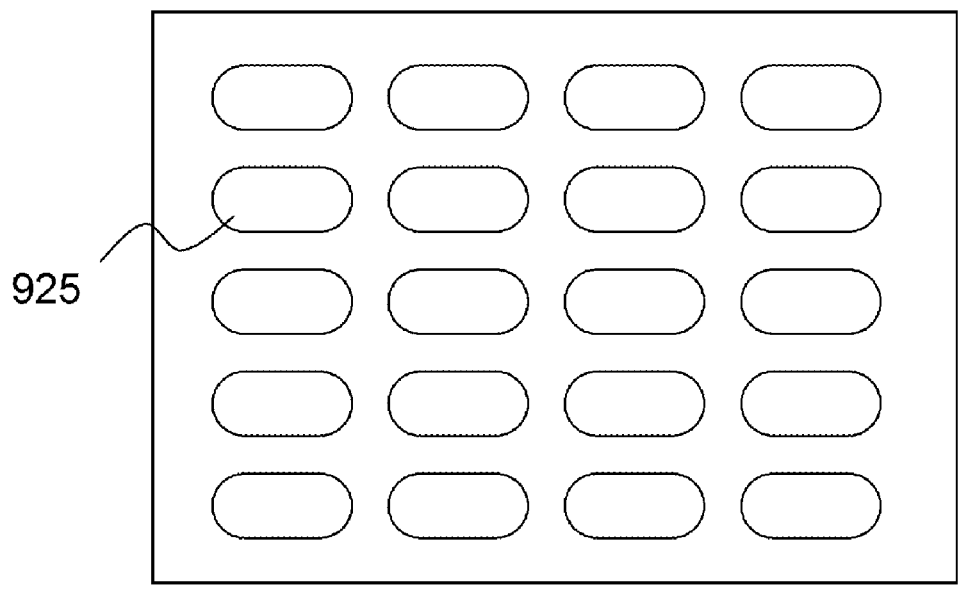
Figure 9D:
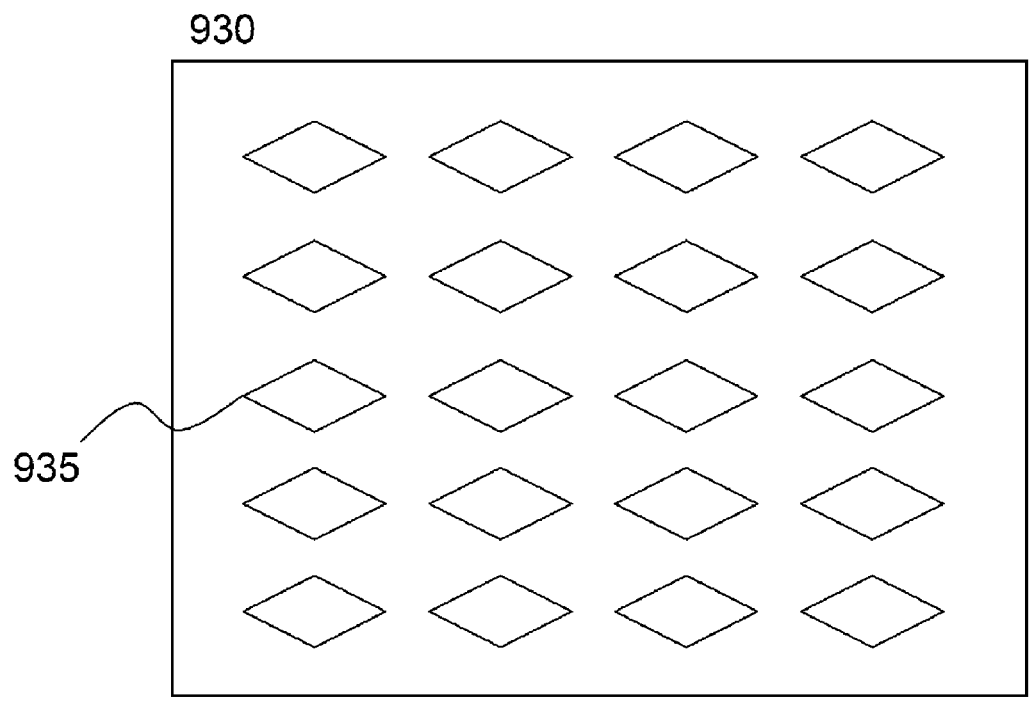
Figure 9E:
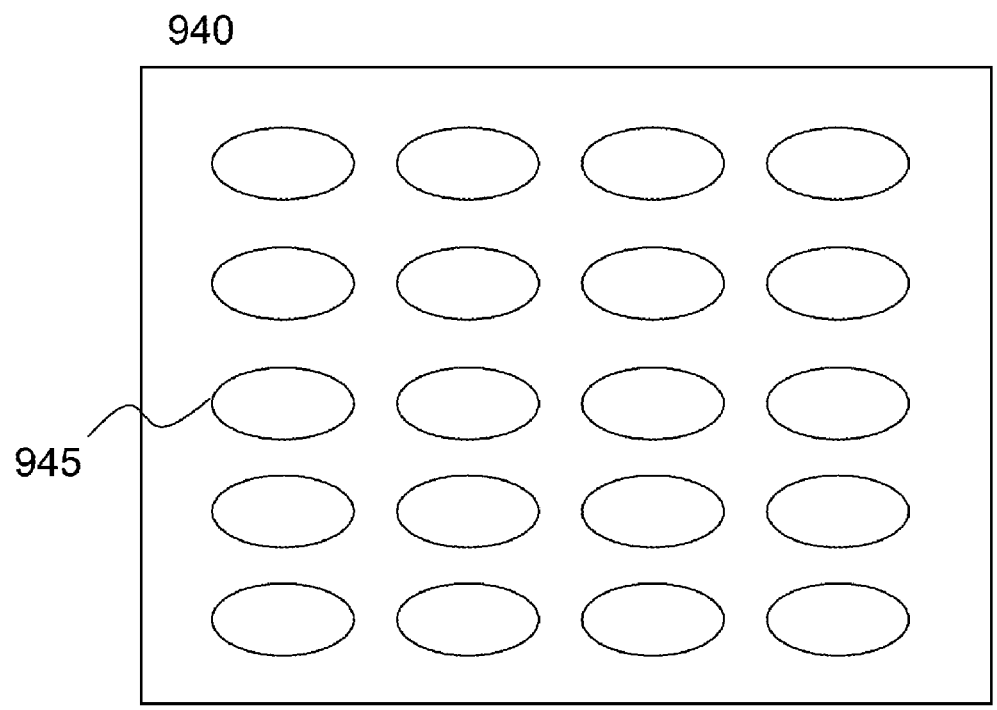

FIG. 9A shows a top view of an array 900 of rectangular nano surface structures 905. FIGS. 9B through 9D show a top view of arrays 910, 920, 930, and 940 of triangular 915, round rectangular 925, diamond 935, and oval 945 shapes of nano rods or nano holes.

Figure 10:
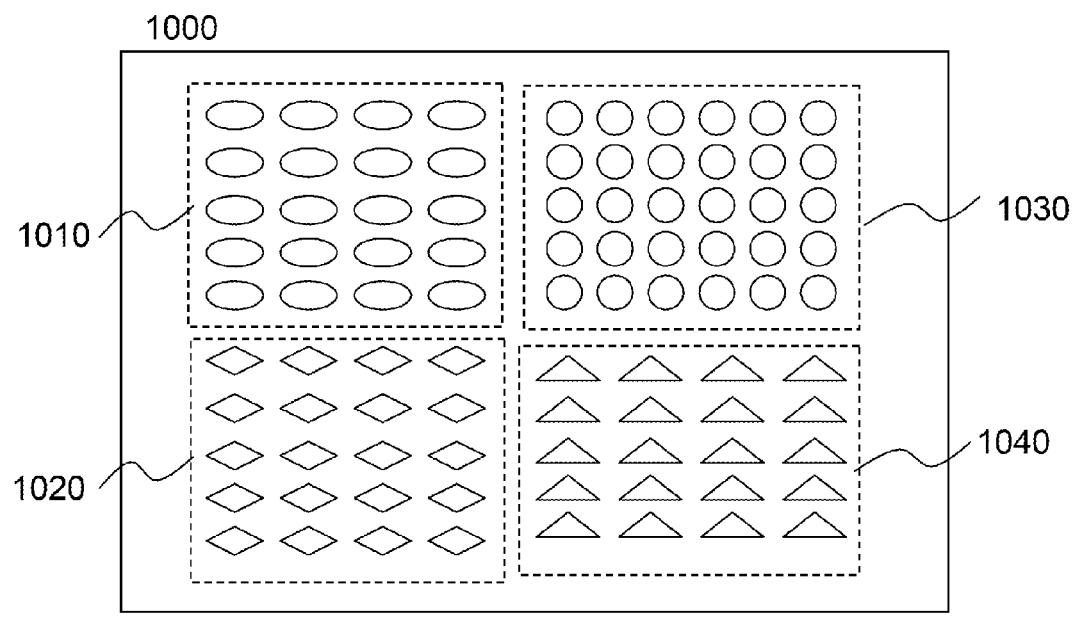
FIG. 10 shows an array comprising sub-arrays with various shapes.
Figure 11:
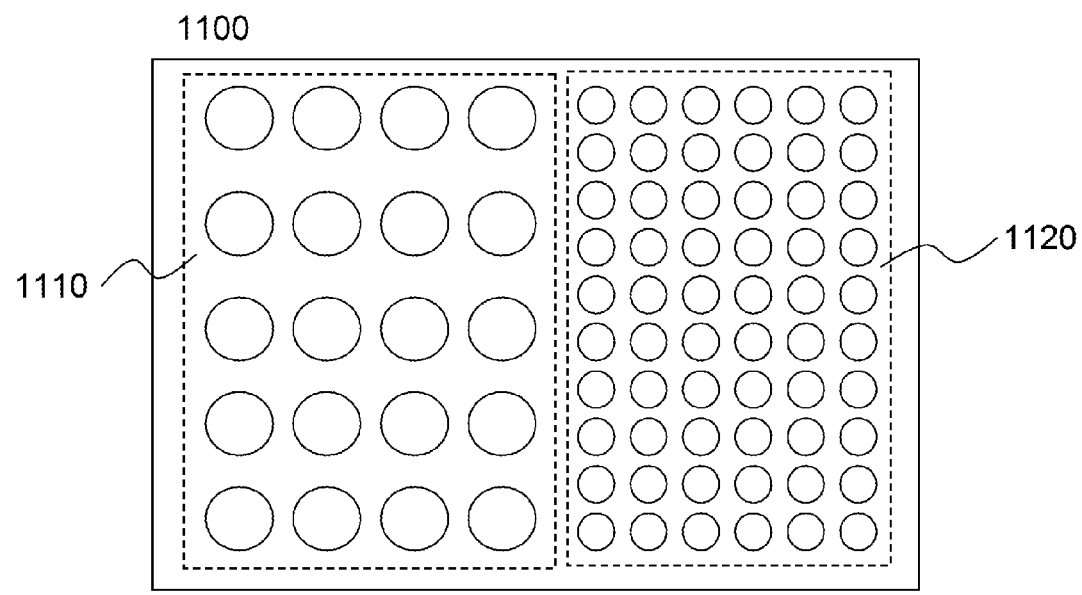
FIG. 11 shows an array comprising sub-arrays with various sizes.

FIGS. 10 and 11 illustrate embodiments that an array device may combine a number of sub arrays. An advantage of using the combination of the sub-arrays is that no optimization of the nano surface structures will be needed for specific chemical measurement by SERS. The combination of different arrays can be used as a general Raman enhancement tool.

FIG. 10 shows a top view of an array device 1000 having sub-arrays 1010, 1020, 1030, and 1040. Each of the sub-arrays has different shapes of the nano structures. FIG. 11 illustrate an array device 1100 having sub-arrays 1110 and 1120. The sub-arrays may have the same shape but have different size.

Figure 12:
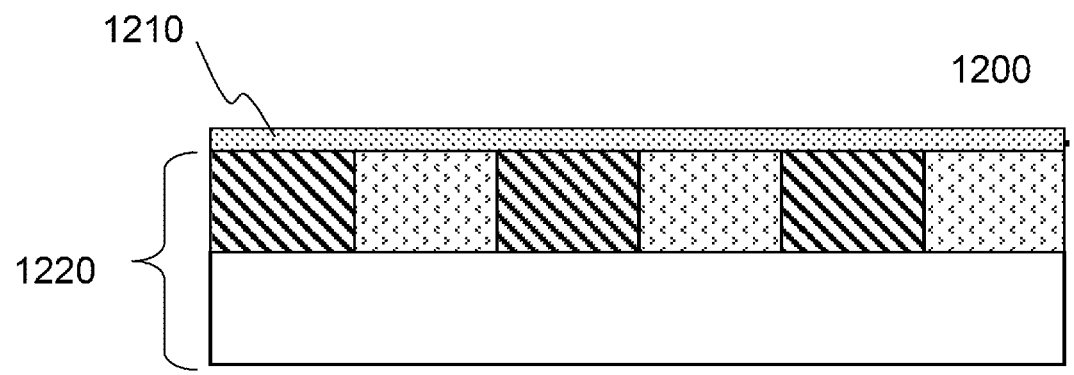
FIG. 12 is a cross section view of an array with a surface adsorption layer over the entire array.

With reference now to FIG. 12, an array device 1200 which has an adsorption layer 1210 over a structure 1220 which is similar to array 200 or 500 shown in FIG. 2 and FIG. 5 respectively. Based on the specific chemical bonding configurations of a measured chemical in SERS, the surface adsorption layer 1210 can be selected with adequate chemical bonds, either positive charged or negative charged, so that the measured chemicals can be adsorbed to the surface, and moved to close to and then adsorbed onto the active areas. The adsorption layer does not need to be very thick. In some cases, a monolayer or even island distributed layer will be sufficient. The layer thickness can be between 0.5 nm and 500 nm, preferred between 2 nm-20 nm. Material suitable for the adsorption layer can include Ag oxide, Au mixed with oxide, $TiO_2$, $SiO_2$, $Al_2O_3$, $Si_3N_4$, $Ta_2O_5$, ZnO, Zr oxide, Hf oxide, Y oxide, Ag oxide, Au oxide, Sn oxide, Sb oxide, or other metal oxide layer, metal layer doped with chlorine or chloride, polymers, etc.

Figure 13:
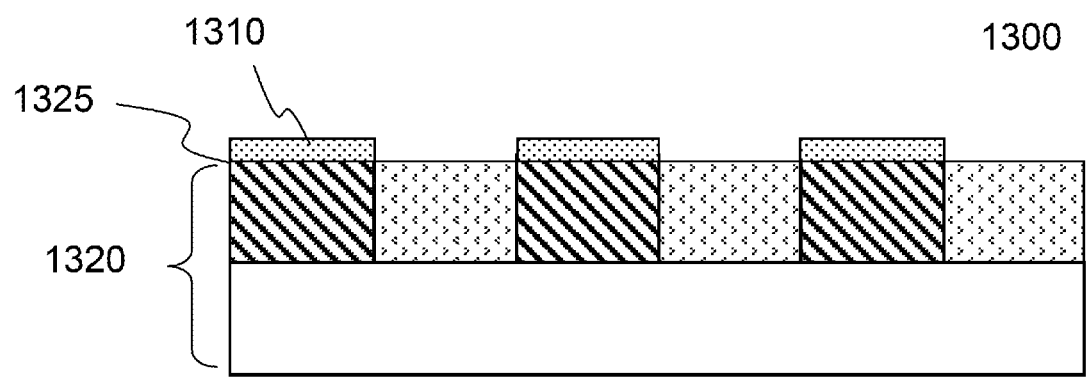
FIG. 13 is a cross section view of an array with a surface adsorption layer selectively covering active SERS nano surfaces.
Figure 14:
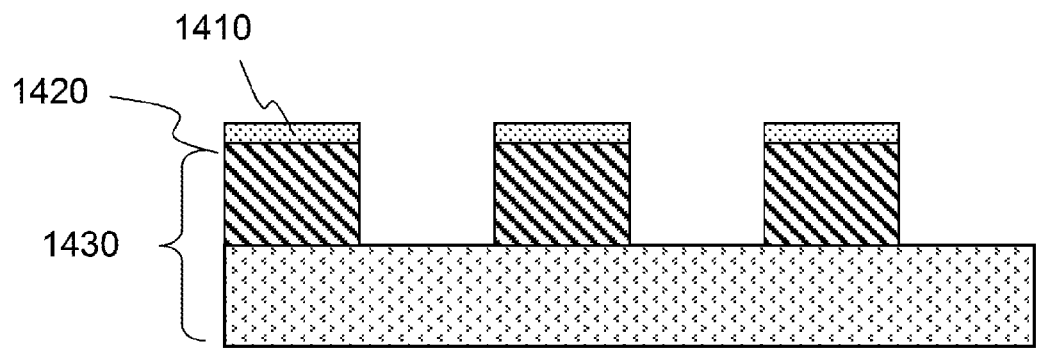
FIG. 14 is a cross section view of an array with a surface adsorption layer selectively covering active SERS nano surfaces according to another embodiment of the present invention.
Figure 15:
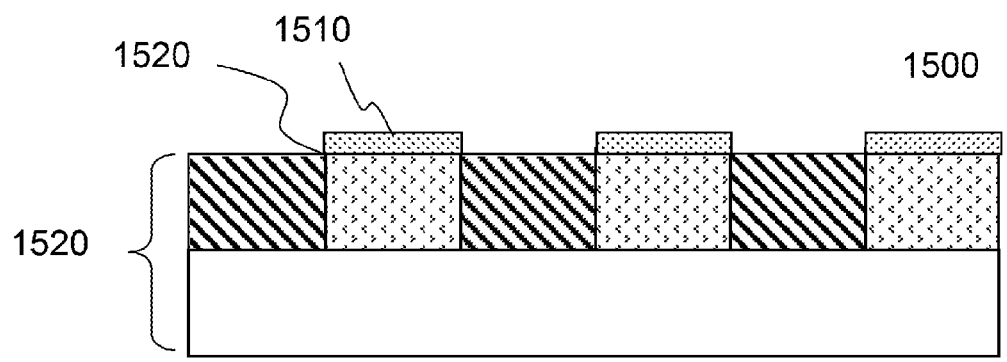
FIG. 15 is a cross section view of an array with a surface adsorption layer selectively covering inactive SERS nano surfaces.

FIGS. 13 through 15 illustrate various arrangement of the adsorption layer over an array device. In one embodiment, the adhesion layer covers only the active SERS nano surfaces.

FIG. 13 shows an array device 1300 having the adsorption layer 1310 disposed selectively on the inactive SERS nano surfaces 1325. The structure 1320 is similar to the array device 200 or 500 shown in FIG. 2 and 5 respectively. Alternatively, an adsorption layer 1410 may be selectively disposed on the active SERS nano surface 1420 for array 1400 shown in FIG. 14.

In another embodiment, an adsorption layer 1510 may be selectively disposed on top portion of the isolated inactive SERS nano surface 1520 as shown in FIG. 15. The structure 1530 is similar to array structure 300 shown in FIG. 3.

There may be other variations of arrangements of the adsorption layer. It is to be understood that the purpose of these arrangements is to bring molecules of an analysis close enough to the active nano SERS surface.

Figure 16:
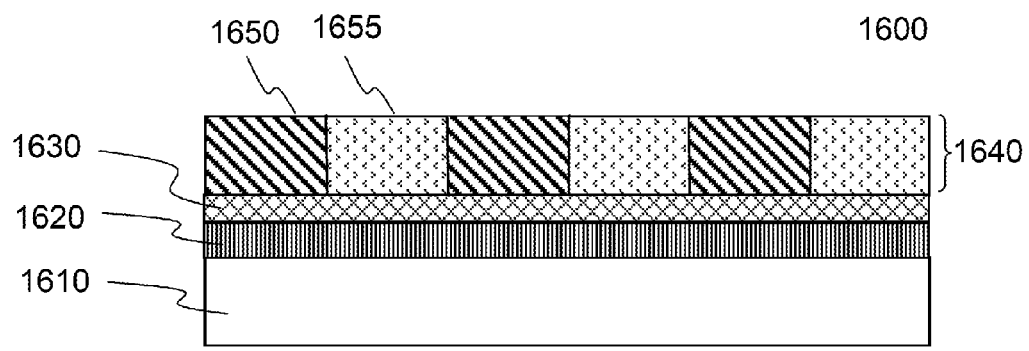
FIG. 16 is a cross section view of an array device with a function layer between a substrate and an array of nano structures.

In some embodiments, an enhancement of molecule adsorption to the device surface is provided by electrical biasing. FIG. 16 shows a device 1600 of an array of nano surface structure 1640 with active and inactive SERS nano surfaces 1650 and 1655 over a metallic layer 1620 on a substrate 1610. There is an optional insulator layer 1630 separating the array 1640 from the metallic layer 1620. Based on the charge states of the measured chemical molecules, a positive or negative bias can be applied to the metallic layer 1620 to attract the molecules to the sensing surface 1650 and 1655.

The metallic layer 1620 is also referred as a function layer. The term, "function layer", as used herein, refers to a layer providing electrical, magnetic, or thermal bias to the array device of nano surface structure.

Figure 17:
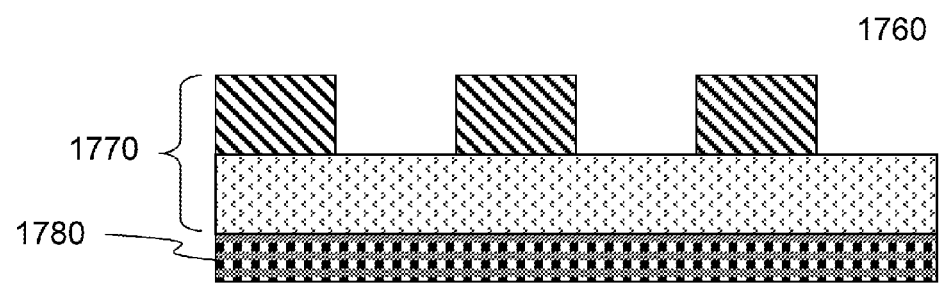
FIG. 17 shows an alternative embodiment of an array device with a function layer.

In some embodiments, molecular adsorption to the device surface can be enhanced by lowering the temperate of the whole array. Giving the array is much thinner than the substrate, a thermal electrical cooler can be connected to the bottom of the substrate (FIG. 17), or to the metal pad area of a sensing chip. FIG. 17 illustrates an array device 1760 where the substrate 1780 is thermally conductive. By applying electrical energy to a cooler, the substrate 1780 including the nano array 1770 can be cooled down to, for example, a temperate range from −20° C. to 20° C. An even lower temperature can be achieved by using a more expensive thermal electrical or other cooler. The lower the surface temperature, the more molecules will be condensed on the surface. By targeting cooled temperature to a sensing chip, selected chemical molecules depending on their boiling temperature would be adsorbed onto the surface.

In some embodiments, the function layer could be used for the purpose of applying a proper DC or AC biasing voltage to the device to attract chemical molecules since many of interested molecules carry positive or negative electric charges. Furthermore, the function layer provides a means to heat the sensing surface to vaporize unexpected/unwanted surface contamination and/or burn out surface contamination. The materials of the conductive layer can be, but not limited to, Ti, Ni, Cr, Pt, Ru, Ni—Cr alloy, NiCrN, Pt—Rh alloy, Cu—Au—Co alloy, Ir—Rh alloy or/and W—Re alloy. This metal must have both good electrical and thermal conductivity, good adhesion to both silicon substrate and metallic sensing surface layer.

In some embodiments, the magnetic field is supplied by the function layer to the sensing chip, or by an external source. In this way, the chemical polar molecules on the sensing surface would have statistically preferred orientation; on the other hand, the chemical polar molecules under test could have their statistically preferred orientation. The effect of applied magnetic field or built-in magnetic materials at function layer is to enhance chemical specific binding, i.e., enhancing chemical molecule adsorption onto the sensing surface, so that to enhance Raman signal.

The direction of applied magnetic field can be parallel to the normal of the sensing surface, and north pole is in front of sensing surface and south pole is at the back of the chip, or north and south reversed; or the direction of the magnetic field perpendicular to it. The magnetic field strength is ranging from 0.5 to 3000 gauss, or 2 to 100 gauss.

Referring now to FIG. 18 through FIG. 21, a number of examples of the array device are depicted. It will be appreciated that the described processes need not to be performed in the order in which they are herein described, but that these descriptions are merely exemplary of preferred methods making the array device. In addition, it is understood and appreciated that the scale of the components and features illustrated in the figures has been exaggerated to facilitate ease of discussion.

Figure 18:
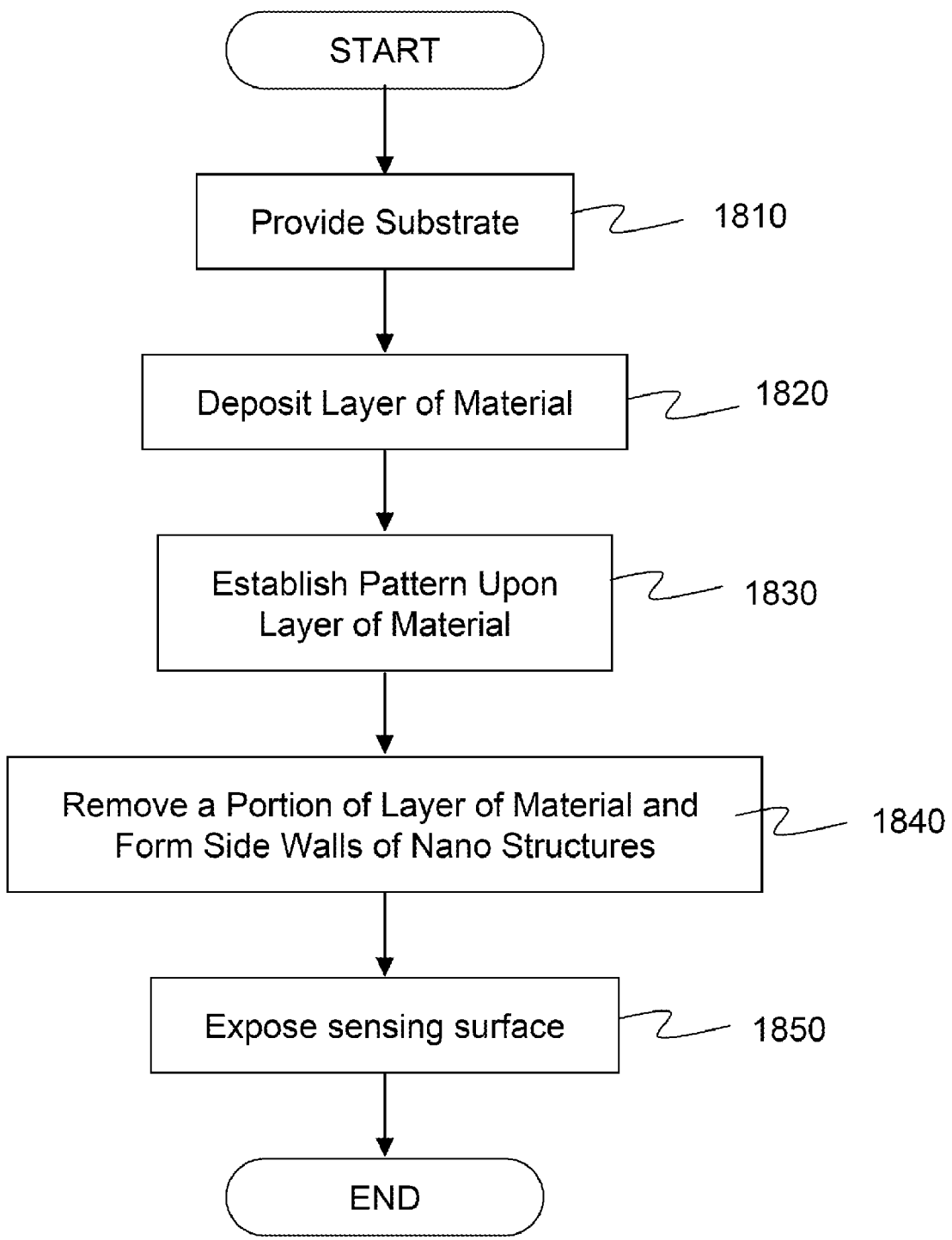
FIG. 18 is a high level flow chart of a method in accordance with an embodiment of the present invention.

FIG. 18 is a high-level flowchart of a method of forming the array device. As indicated in block 1810, the processes are generally commenced by providing a substrate. In at least one embodiment the substrate is a Si wafer. An inactive material may also be used as the substrate. At least one layer of material is deposited upon the substrate, block 1820. A pattern is then established upon the layer of material, block 1830. The pattern provides areas defining a plurality of nano structures. As in block 1840, a portion of the layer of material are removed, so that side walls of the nano structures are formed. The method further includes forming an exposed sensing surface upon the nano structures, wherein said surface comprises at least one active SERS nano surface and at least one inactive SERS nano surface established in proximity to the active nano SERS surface.

Turning to FIGS. 19A to 19D, provided is a more detailed illustration of one process in according to the present invention. The substrate 1900 is made from an inactive material. Alternatively, the substrate can be a non-inactive material with a coating of a layer of an inactive material to provide the inactive SERS nano surface for the completed device.

Figure 19A:
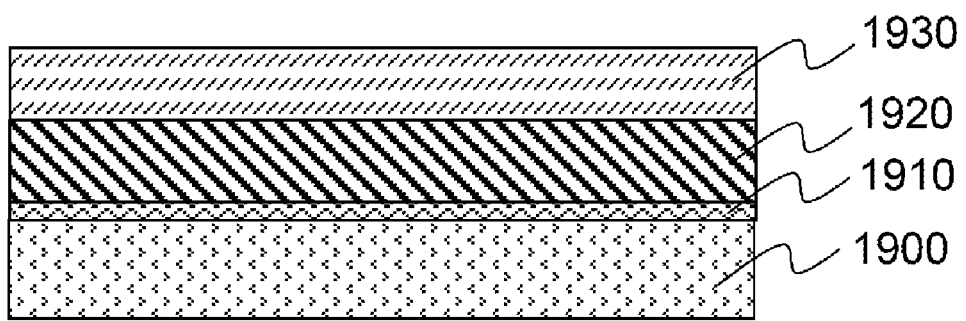
FIG. 19 shows a process for forming an array device in accordance with an embodiment of the present invention.

As shown in FIG. 19A, a layer of adhesion layer 1910 is deposited upon the substrate to adhere nano structures onto the substrate. Non-limiting examples of materials for the adhesion layer are Ti and Ni. The thickness of the adhesion layer is between 10 to 100 nm. This layer is optional. A device may be made without this layer.

Upon the adhesion layer, a layer of active material 1920 is deposited thereon. The thickness of the active layer 1920 is between 1 nm to 5 μm. In an embodiment, the thickness of the active layer 1920 is between 5 nm to 100 nm. A mask layer 1930 is then deposited on the layer of active material 1920. An example of the mask layer is a layer of photoresist or e-beam resist. An optional metal layer may be established between the resist layer 1930 and active layer 1920 to serve as a hard mask in subsequent processes.

Figure 19B:
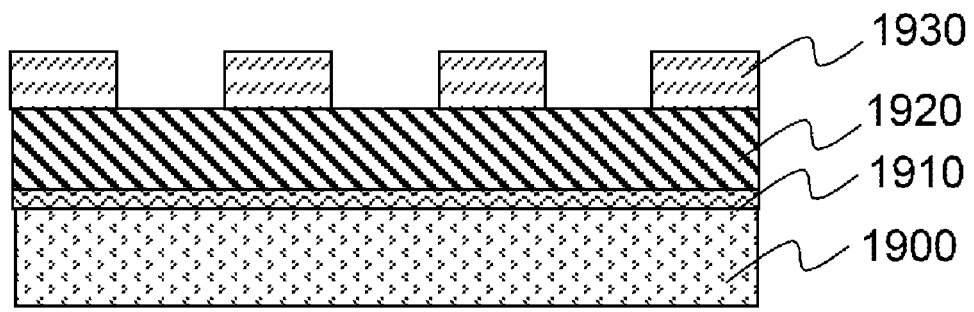

Next, a pattern on the resist layer 1930 is established by a photolithography process or e-beam process (FIG. 19B). Photolithography and e-beam patterning techniques are well known to those skilled in the art and commercially available and need not be described in more detail herein.

Figure 19C:
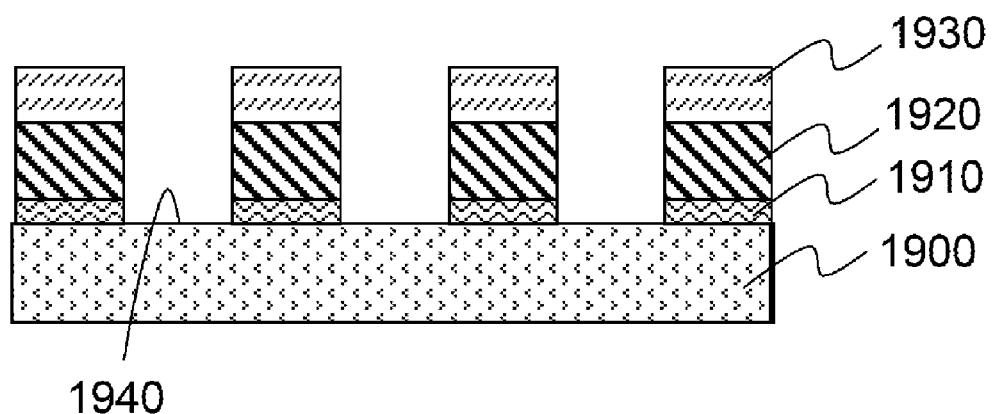
Figure 19D:
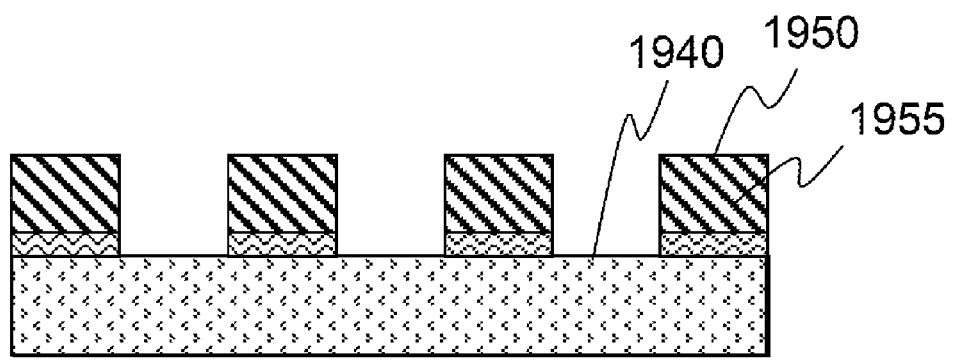

Next, the exposed portion of the active material and the adhesion layer are removed by etching processes such as wet chemical etching or plasma etching (FIG. 19C). The inactive SERS nano surfaces 1940 are formed around nano rods 1955. The remaining mask layer 1930 is finally removed. As shown in FIG. 19D, the completed device has a plurality of nano rods with the active SERS nano surfaces 1950 formed on the top and side wall surfaces of the rods. These active surfaces are surrounded by the exposed inactive SERS nano surface 1940.

In an alternative embodiment, layer 1900 can be an active material and layer 1920 can be an inactive material. Following the above detailed process, a device with an array of nano rods of the inactive material will be produced. The inactive SERS nano surfaces will be surrounded by the active nano SERS surface.

Figure 20A:
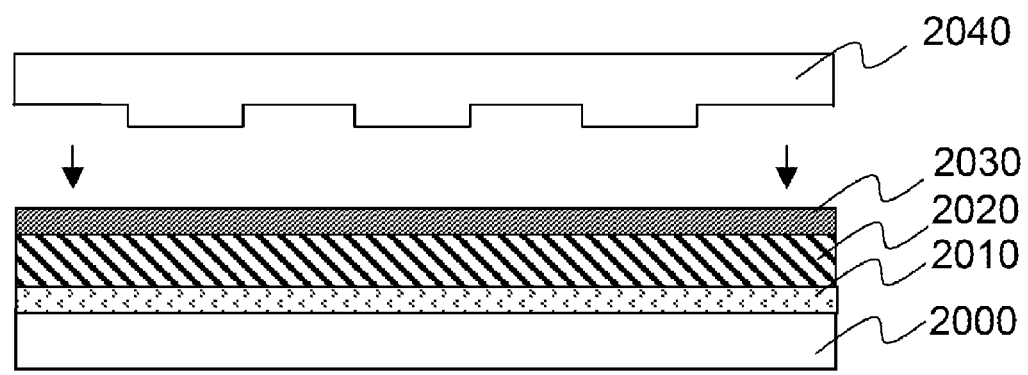
FIG. 20 shows another process for forming an array device in accordance with an embodiment of the present invention.
Figure 20B:
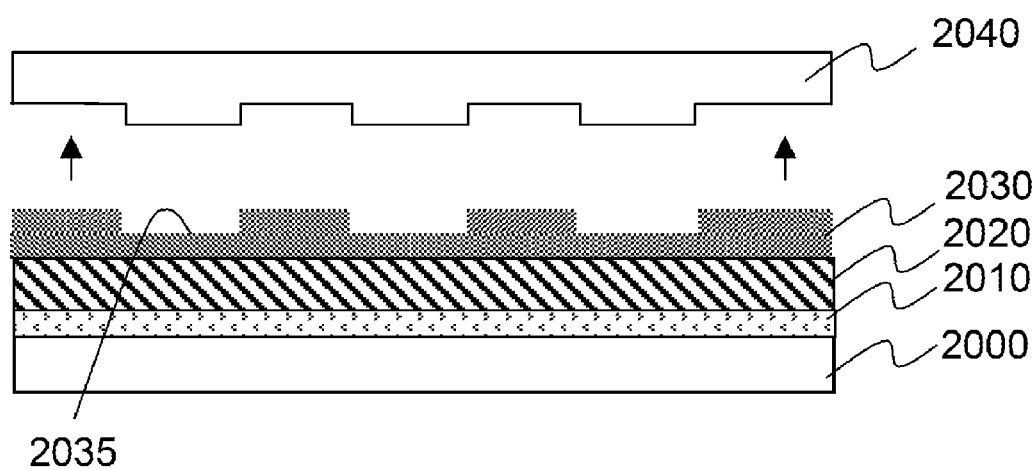
Figure 20C:
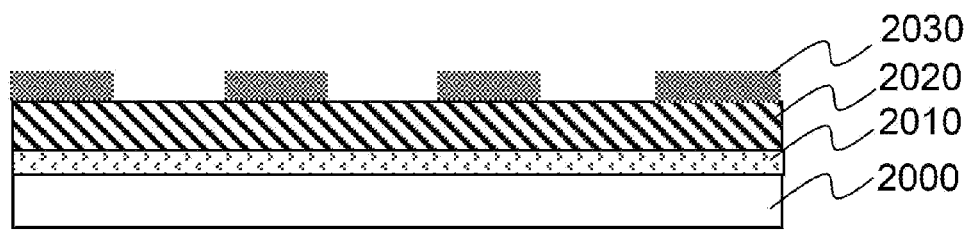
Figure 20D:
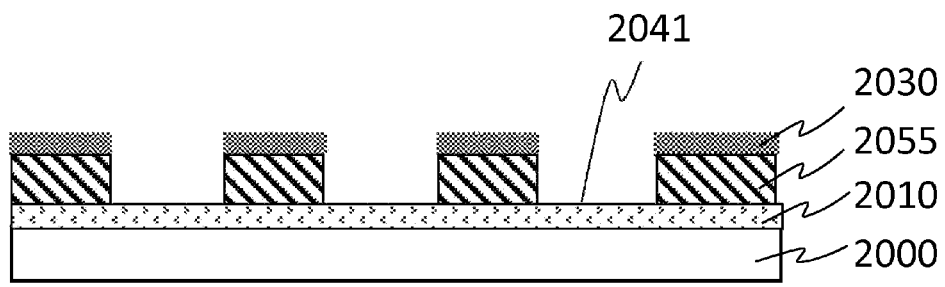
Figure 20E:
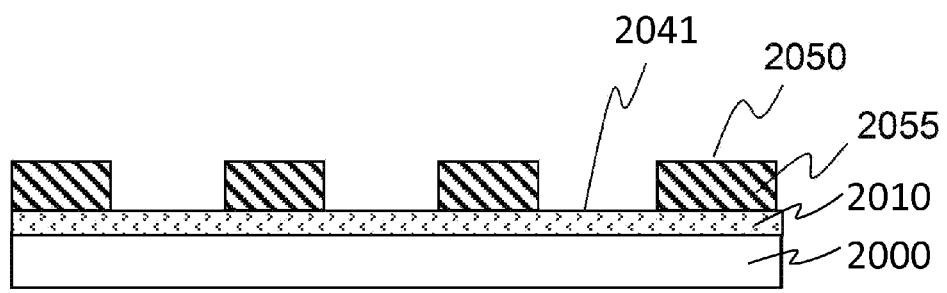

A sequence of steps of yet another embodiment of forming array device is shown in FIGS. 20A through 20E. A pattern of the nano structures is defined by an imprint lithography process. The pattern can be produced on a substrate such as a silicon wafer by e-beam lithography and reactive ion etching. The patterned substrate can act as a mold. The pattern in the nano scale is a reverse image of a final nano array. In the first step, a layer of inactive material 2010 may be deposit onto the substrate 2000 to establish the inactive nano SERS surface. A layer of active material 2020 such as Ag or Au is then deposited onto the inactive layer. Then a layer of imprintable material 2030, such as a PMMA or other polymer, is coated on layer 2020. The mold 2040 is then pressed into layer 2030 (FIG. 20A). Imprinting is made during the step after removing the mold (FIG. 20B). In FIG. 20C, pattern transfer is complete using etching to remove residual resist 2035 in the compressed areas. Further chemical etch can be used to etch the metal film in the compressed areas (FIG. 20D). An array of nano surface structure is produced after removing the mask layer. As shown in FIG. 20E, the completed device has a plurality of nano rods 2055 with the active SERS nano surfaces 2050 formed on the top and side wall surfaces of the rods. These active surfaces are surrounded by the exposed inactive SERS nano surface 2041.

Figure 21A:
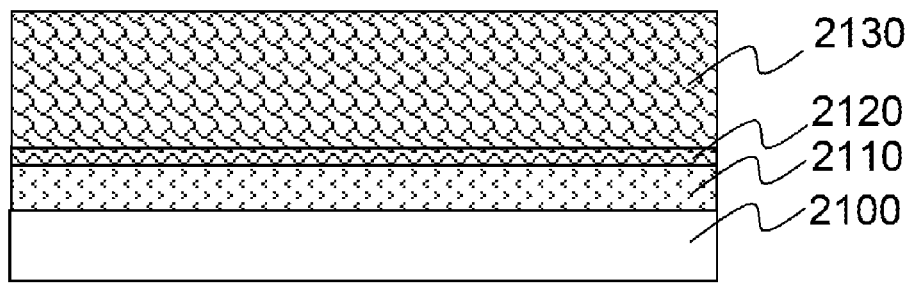
FIG. 21 shows yet another process for forming an array device in accordance with an embodiment of the present invention.

FIGS. 21A to 21D provide another embodiment of forming array device. In this embodiment, an array of nano structure is defined by an anodization process. FIG. 21A shows a stack of layers deposited on a substrate 2100. The substrate 2100 may be a silicon wafer. The first layer 2110 is an inactive material. This layer can be 30-50 nm $SiO_2$ made by oxidizing silicon wafers. Above the inactive layer, an adhesion layer 2120 is deposited. The thickness of the adhesion layer is usually controlled in the range of 100 Å-1,000 Å and optimized to provide best adhesion to a noble metal layer, e.g., an Ag or Au layer. The thickness of the adhesion layer 2120 is also optimized for applying an electric bias to the sensing surface for trace chemical detection and further for applying a lower temperature to the sensing surface to enhance sensitivity of trace chemical detection. Above the adhesion layer, an aluminum layer 2130 with a thickness in the range of 0.5-10.0 micrometers, is deposited. Then an anneal operation is performed on the aluminum layer 145 to recrystallize the Al film.

Figure 21B:
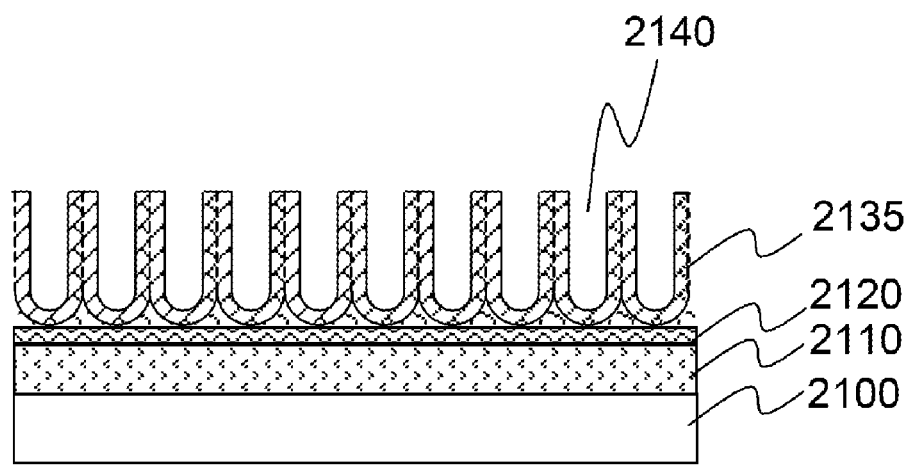
Figure 21C:
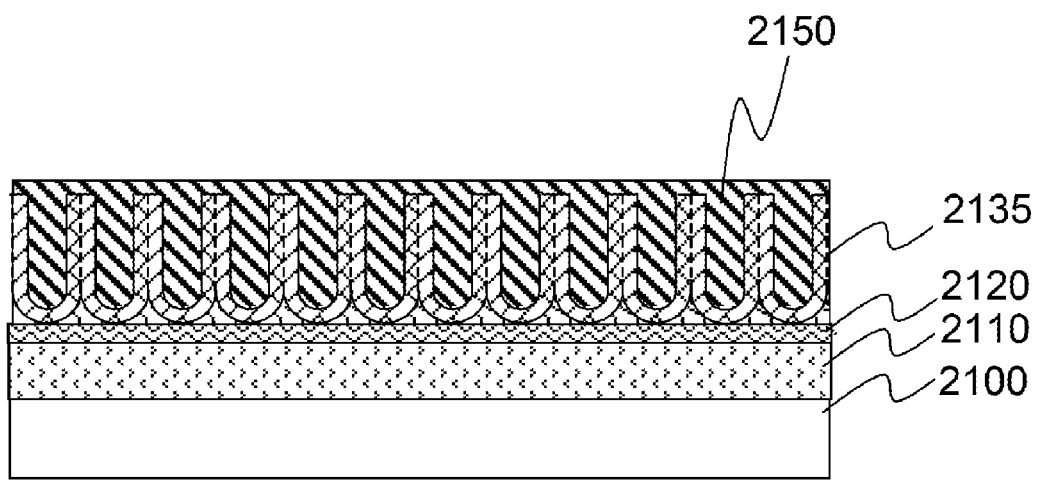

Next, an anodization process is carried out to produce a porous structure 2140 in a form of porous aluminum oxide 2135 (FIG. 21B). In the anodization process, the nano hole or rod diameter d, nano hole or rod spacing/neighboring distance D, and depth of nano hole array or height of nano rod array can be controlled and modified by adjusting operation voltage, current, chemical solution pH value and temperature and process time, etc. The porous structure is formed with naturally self-assembled hexagon-shaped nano pore-array that includes a plurality of pores 2140 surrounded by hexagon-shaped pore wall. Then a wet etch process is performed to widen the pores 2140 and to remove the barrier layer at the bottom of the pores.

Figure 21D:
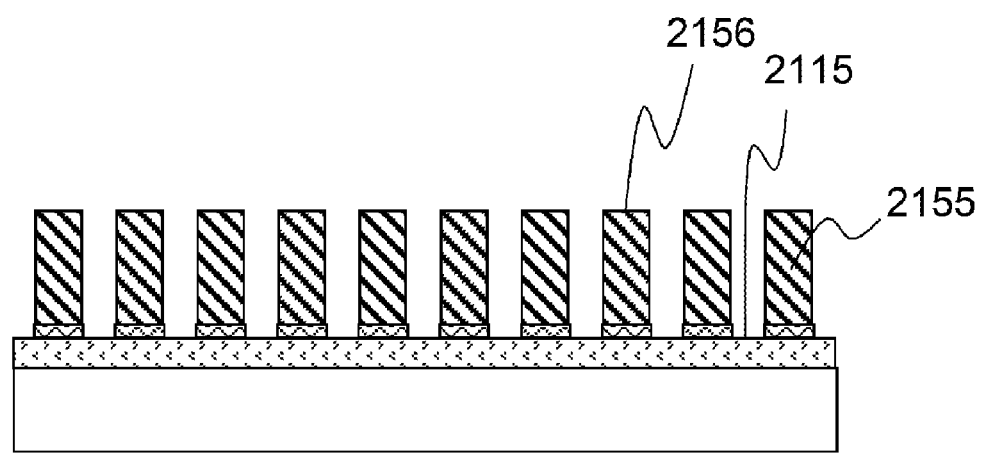

Next, an active material such as a noble metal 2150, such as Ag, Au, or Cu, is deposited to fill the plurality of pores by any physical, chemical, or electrochemical methods. (FIG. 21C) A chemical process is then performed to remove the top portion of the noble metal 2150 and the aluminum oxide 2135. A plurality of noble metal columns 2155 are formed on top of the adhesion layer 2120. The exposed portion of the adhesion layer is removed to expose the inactive SERS nano surface 2115 (FIG. 21D). The completed device has a plurality of nano rods with the active SERS nano surfaces 2156 formed on the top and side wall surfaces of the rods. These active surfaces are surrounded by the exposed inactive SERS nano surface 2115.

Figure 22:
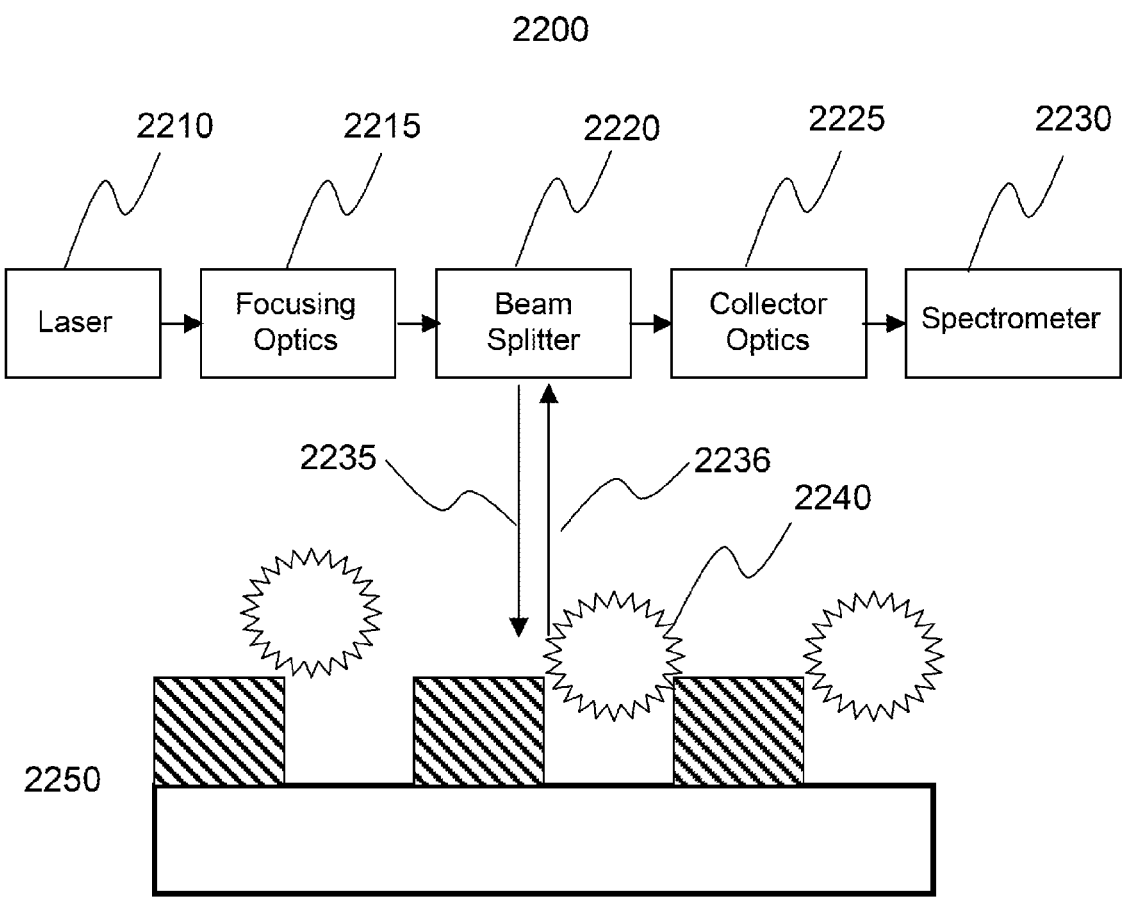
FIG. 22 is a diagram of a SERS system using an array device in accordance with an embodiment of the present invention.

Referring now to FIG. 22, provided is an illustration of a trace chemical detection system based on the array device in accordance with one embodiment of the present invention. The system includes surface-enhanced Raman spectroscopy (SERS), surface-enhanced Raman resonance spectroscopy (SERRS), surface-enhanced coherent-anti stokes Raman scattering (SECARS), surface-enhanced infrared absorption (SEIRA) spectroscopy, surface-enhanced fluorescence spectroscopy (SEFLS), surface-enhanced photoluminescence spectroscopy (SEPLS), time-resolved above mentioned spectroscopies, other optical spectroscopic methods, and combination of above listed methods, for example, SERS combine with SEFLS or SERS combine with SEPLS, for chemical fingerprint identification and trace chemical sensing.

As shown in FIG. 22, the system 2200 comprises an optical source 2210 such as a laser beam source and an optical assembly 2215 to focus the laser beam. The beam is then deflected by a deflector 2220 to irradiate an array device 2250. The array device 2250 is adsorbed with a chemical substance which is going to be analyzed. Molecules 2240 of the chemical substance adsorbed on the sensing surface of the array device scatter the incoming beam 2235. A portion of the scattered photons 2236 are collected by an optical system. A spectrum analyzer, such as a spectrometer, receives said portion of scattered photons and generates an output indicative of the composition of the chemical substance.

The system illustrated by FIG. 22 can be used in chemical fingerprint identification and trace chemical sensing in the areas of medical/health care, life science, environmental, food safety, forensic, homeland security, etc. For homeland security application at the areas including but not limited to airports, customs, cargos, harbors, trains and train stations, subways, buildings, shopping malls, theaters, resort centers, surface water and other water supply system including wells, the dangerous and harmful chemical compounds can include explosives, nerve agents, blood agents, blister agents, heavy metals and other poison chemicals, e.g., Pb, Cd, Hg, Tl, and arsenic contained compounds, volatile toxins, e.g., benzene, chloroform, pulmonary agents, e.g., phosgene, vinyl chloride, biological agents, toxins, and nuclear weapons. The explosive substances can include TNT, DNT, MNT, DNB, DMNB, EGDN, NG, RDX, PETN, TATP, TATB, HMX, ammonia nitrate, tetryl, picric acid, HNS, etc., and mixtures of two or more items mentioned above, for example, C-4, etc. The dangerous chemical substances also include nerve agents including but not limiting to tabun (GA), sarin (GB), soman (GD), GF, and VX, etc. The blood agents can include cyanides (cyanogen chloride (CK), hydrogen cyanide (AC), potassium cyanide (KCN), sodium cyanide (NaCN), etc.), arsine (SA). The blister agents can include but not limiting to lewisite, phosgene oxime (CX), mustards, etc. The biological agents can include category A agents, e.g., anthrax, smallpox, plagues, category B agents, e.g., Q fever, category C agents, e.g., yellow fever.

The system based on the array device in accordance of the present invention can also be used in chemical fingerprint identification and trace chemical sensing in environmental application, for example, toxic materials monitoring and screening, including but not limited to inorganic and organic nitrites and chlorine contained chemicals, such as NO2— and ClO4— groups and dioxins, benzene and its derivatives, cyanides, heavy metals including but not limited to Pb, Cd, Hg, and arsenic contained compounds, and residue pesticides, and other toxic chemicals in ocean, lake, rivers, reservoir, and wells, and other surface and underground water, as well as in soul and in air.

For environmental protection, the disclosed chemical sensing system can be used for outdoor and indoor pollution monitoring and screening emission sources. Outdoor pollution includes auto vehicle exhaust gas, factory exhaust gas and liquid, etc. Indoor Pollution monitoring and screening in both family houses and workplaces, including but not limited to building, airplane, space shuttle, boat and ship, submarine, and all other areas under the ceiling. Application includes but not limits to monitoring and screening air quality and other health problems associated with plastic floor, wall painting and decoration, painted furniture, plastic household, tools, toys and all other plastic materials indoor which may contain toxic materials, for example, benzene, its derivatives and other volatile organic compounds (VOC), polyvinyl chloride (PVC) and its additives including phthalate, DEHA, and heavy metals, etc.

For medical applications, non-invasive or minimal-invasive early disease diagnosis can be accomplished using the disclosed array device in accordance of the present invention. For example, test through human skin test, eye test, or body fluid test, including saliva, sweat, blood, and urine test, and human breath test to early detect diseases, including but not limited to lung cancer, breast cancer, oral and head cancers, ulcer, bronchial, oesophageal and stomach cancer, colon cancer, skin cancer, diseases of liver, kidney, pancreas, bladder, prostate, uterine, esophageal disease, oxidant stress, eye disease, diabetes, schizophrenia, lipid peroxidation, asthma, tuberculosis, helicobacter pylori, etc. Noninvasive or minimal-invasive test can be also applied to diagnose Alzheimer's disease.

The disclosed systems and methods are applicable to urine test by "Smart Toilet" equipped with SERS sensor to early detect diseases, including but not limited to prostate cancer, diseases of bladder, uterine, etc., and to monitoring and screening drugs.

The disclosed systems and methods are applicable to human and animal body fluid test. For example, saliva test for oral cancer, blood test for early disease diagnosis, including but not limit to Alzheimer's disease, HIV, mad cow disease, cardiovascular disease, cancers, and Fast virus and bacteria identification and screening, including but not limited to SARS, bird flu, smallpox, HIV, etc.

Raman diagnosis method can be applied to real time doctor visiting procedure, such as disease screening or special disease diagnosis. In this way, doctor is able to make judgment based on real time Raman test during patient visit, and make on timely decision for necessary medical treatment.

The disclosed systems and methods can be used during surgery, real-time in-line identify cancer tumor portion, rather than usually applied biopsy method which requires time, distinguish the boundary between cancer tumor portion and health portion to real-time support doctor to make decision on cutting location.

The disclosed systems and methods can be used in pharmaceutical applications in medicine R & D, manufacturing and quality monitoring. Raman method can be also applied to medicine taking feedback process. For example, before patient taking medicine and after patient taking medicine at different period of time, Raman test can be carried out to investigation effectiveness from medicine.

The disclosed systems and methods are compatible with a miniaturized Raman sensor with wireless technology used inside human body. For example, a system-on-chip Raman system can be made in a tablet size which includes on-chip mini-laser source, MEMS based mini-spectrometer, wireless module, mini-probe, etc. Initial application will be disease diagnosis of digest system. For example, patient or a person being screened swallows a tablet sized Raman system after his/her digest system got cleaned (similar procedure to that of preparation for colon endoscopy test), Raman scans will be taken timely, for example, from every one minute to every hour a time, then data will be transferred by wireless module, and a computer outside human body will receive Raman data and analyze, search, match, then decision making; next stage of application is minimal invasive with a needle shaped probe head to bring mini-Raman sensor into diagnosis area inside human body, Raman data can be transferred through optic fiber, or wireless module. Applications include but not limit diagnosis of breast cancer, Alzheimer's disease, etc.

The disclosed systems and methods can be used in biotechnology and biomedical applications, such as fingerprint identification of DNA, RNA and protein, DNA sequencing, DNA sorting, etc.

The disclosed systems and methods can be used in forensic applications such as drug test and screening through saliva test, urine test, or powder test; false signature recognition; human identification and screening by DNA profiling; identify microscopic paint fragments, fiber identification, etc. The disclosed systems and methods can be used in drug screening through human body fluid test, or/and breath test by Raman method based on the array device in accordance of the present invention is developed.

The disclosed systems and methods are applicable to food, fruit and beverage monitoring and screening application, monitoring of chemicals in gas, liquid, power, gel, aerosol, or solid phases, including but not limited to ethylene, for stored fruits and vegetables with longer shelf time application; food safety, monitoring and screening harmful chemicals including but not limited residue pesticides (e.g., methamidophos, cypermethrin, deltamethrin, malachite green, etc.), dioxins, illegal artificial additives (e.g., Sudan I, Sudan II, Sudan III, Sudan IV, etc.), food processing by-products (e.g., acrylamide formed from potato chips from processing temperature over 120° C.) by Raman method based on the array device in accordance of the present invention is developed. Those chemicals include but not limit to acrylamide, malachite green, etc. Foods under investigation include but not limit to potato chips, French fries, fried potato, potato crisps, cookies, crackers, cereal products, crisp bread, bread, coffee, prepared toast, roasted nuts, biscuits, chocolates, popcorn, and aquatic products including fish, etc.

The disclosed systems and methods are applicable to identifying and monitoring food packaging processing and preparation materials, including but not limited to identify and screen polyvinyl chloride (PVC) and phthalate materials used as the microwave food wrap, kitchen film, food packaging, processing and preparation materials.

The disclosed systems and methods are applicable to screening counterfeit merchandizes and materials, including but not limited to medicines, drugs, milk-based powders, edible oil, wines, gemstones, currency bills, false signature through inks, art pieces, gasoline, etc.

The disclosed systems and methods are applicable to industrial process quality and production safety monitoring. Application areas include but not limited to process control for product quality, process and production safety at gas and wet chemical process lines, for example, petroleum refinery plant, chemical engineering manufacturing plant, semiconductor wet chemical process line in clean room, airline and space shuttle, boat, ship and submarine, etc.

The disclosed systems and methods are applied to determine the locations of chemicals. For example, a sensor or sensor network can be placed at different locations including but not limiting to medical doctor clinic office, surgery operation room, shopping center, public resort area, building, custom, road check station, harbor, airport, vehicle, boat and ship, airplane, space shuttle, industrial process site, R&D research lab, quality control office, college lab and office, surface water, well, ground water, hand carried by operation people, and so on.

Chemical sensing application engineering, not only single chemical sensor is placed on site, but chemical sensor net work is designed and arranged to cover application area which all sensors are controlled by sub-central controllers and main-central controller connected with fiber optic or/and wireless system. When abnormal result is found, an alarming signal is automatically triggered in the forms including but not limiting to red color blinking on screen of a computer or PDA, alarming sound in key area, sending alarming E-mail to key people, triggering a phone call to key people cell phone, etc. The abnormal result can be classified into different risk level, for example, green (safe), blue, yellow, orange, red (the most risk).

EXAMPLES

The invention will be further described in the following examples, which do not limit the scope of the invention described in the claims.

Example 1

Fabrication of Nano-Surface Arrays by Anodization Method

A thin film of Ti (about 100 nm) was deposited by e-beam evaporation of Si (100) wafer, followed by the deposition of Ag (about 100 nm). Then a 500 nm Al layer was deposited over the Ag film using physical vapor deposition method.

Then the coated Si wafer was placed into an anodizing bath with 0.3 M oxalic acid solution as the electrolytic solution. The bath was maintained at 10° C., and the anodizing voltage was set at 35 V. After anodization, nano-size narrow pores were formed in the $Al_2O_3$ layer. The diameter of the pores (or holes) can be widened by placing the wafer into a 10 wt. % phosphoric acid solution. The nano pore structure in the $Al_2O_3$ layer acted as a mask for etching active metal layer or depositing active metal layer. Thus a nano surface array was formed after removing oxidized Al layer.

Example 2

Nanoimprint Lithography for Fabrication of Nano-Surface Arrays

The first step in nanoimprint is to press a mold into a thin resist cast on a substrate. The step is to duplicate the nano-structure on the mold in the resist film. The second step is to etch the resist film to form the nanostructure on the substrate.

The mold was patterned with an array of nano dots of 30 nm in feature size using electron beam lithography and reactive ion etching (RIE) on a Si wafer. PMMA was used as the resist on Au coated Si (100) wafer. A thin Ti layer was inserted between Au and Si to improve adhesive. The imprint process was carried out in vacuum at a temperate around 160° C., above the glass temperate of PMMA, at a pressure about 1000 psi. After the pattern from the mole was transferred to the Au coated Si (100), oxygen RIE was used to remove residue resist in the compressed areas in PMMA. Then, the pattern was etched into the Au film. After removing the PMMA, a nano-hole array was formed in Au.

Example 3

1) Demonstration of Nano Array

Figure 24:
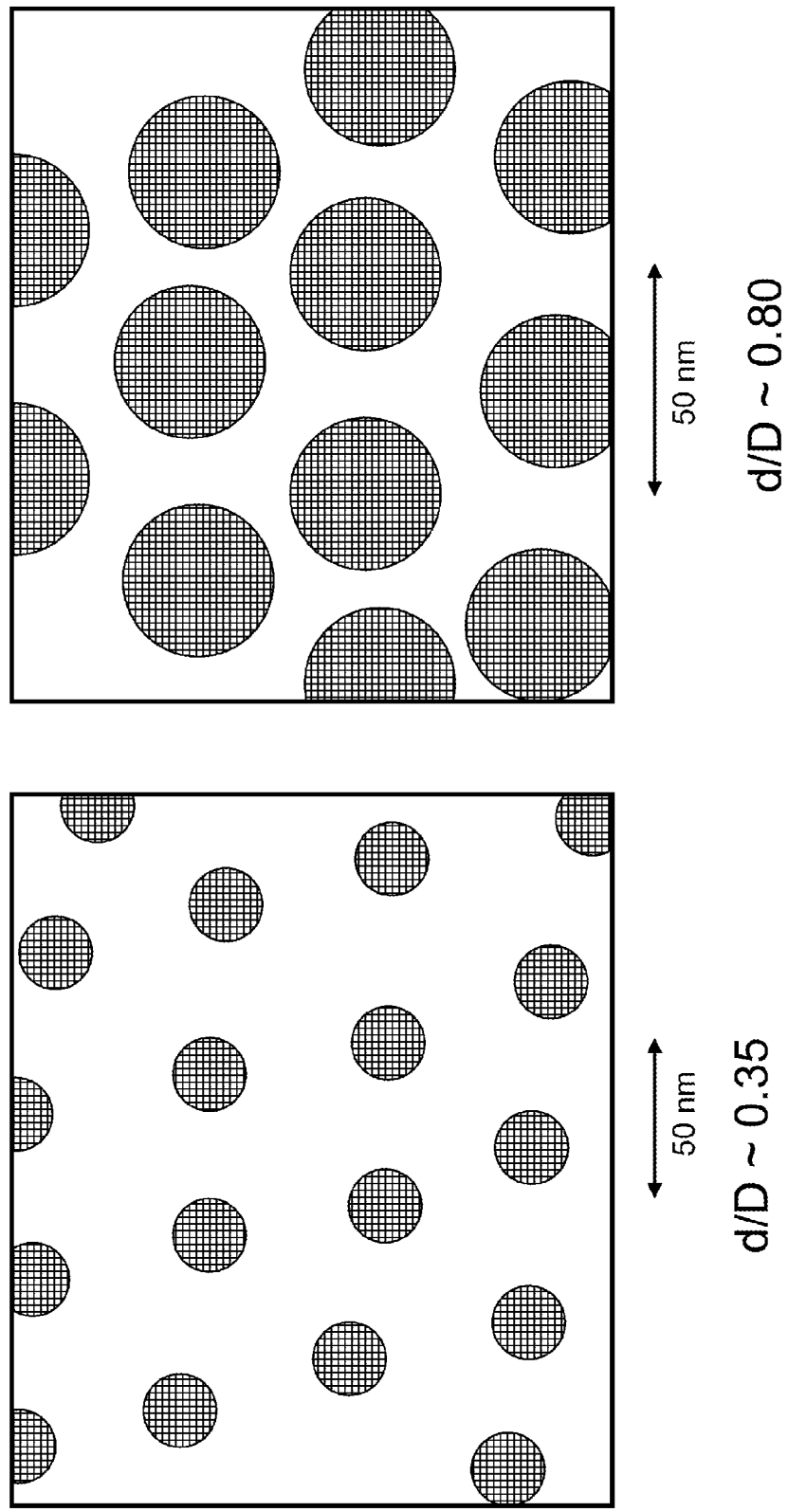
FIG. 24 shows scanning-electron micrographs (SEM) of top-view of a surface structure, where d is the averaged diameter of nano holes, and D is the averaged center-to-center distance between adjacent nano holes.

FIG. 24 is an example of scanning electron microscopy imaging of such nano surface arrays. The left image shows an array of nano-holes with 17 nm diameter and about 30 nm spacing. The image on the right shows an array of nano-holes with 38 nm diameter and about 10 nm spacing.

2) Demonstration of Surface Enhanced Raman Using the Nano-Surface Arrays

Figure 23A:
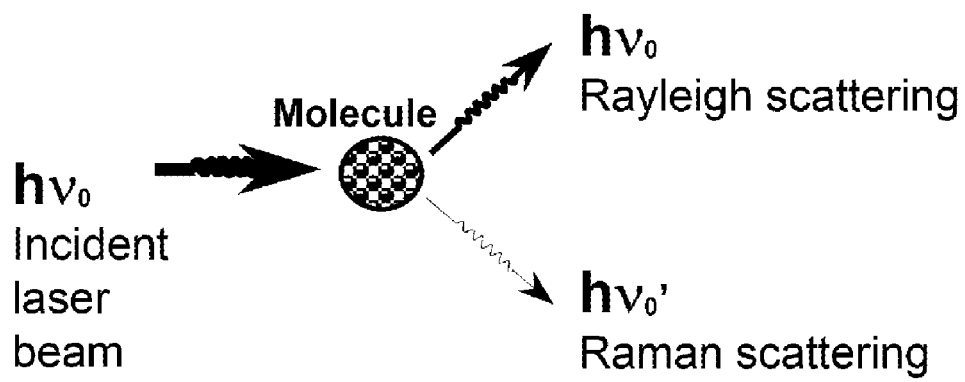
FIG. 23 shows a schematic Raman experiment setup and Raman spectra of various chemicals.
Figure 23B:
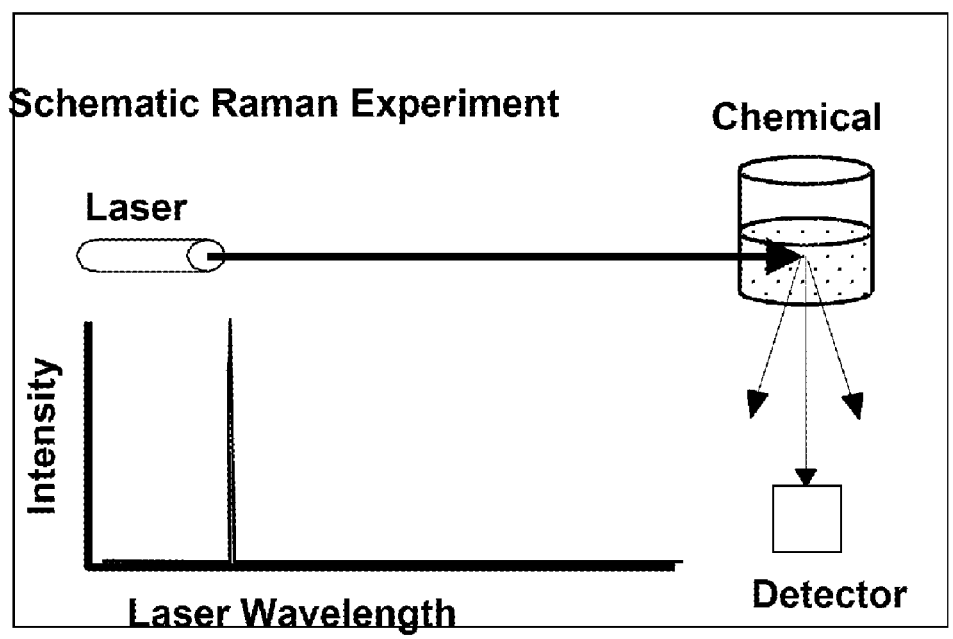

A Raman scattering setup (FIG. 23B) consisted of a Raman nano-surface array on silicon, a semiconductor laser, and collect the reflected lights on the surface. The sampling methods include: the array is placed in a solution container or a gas probe cell; or is just lie down horizontally, then to inject liquid chemical onto the surface; or the array is covered by a layer of glass or polymer without physical contact, liquid or gas sample is injected through a microfluidic channel.

Figure 23C:
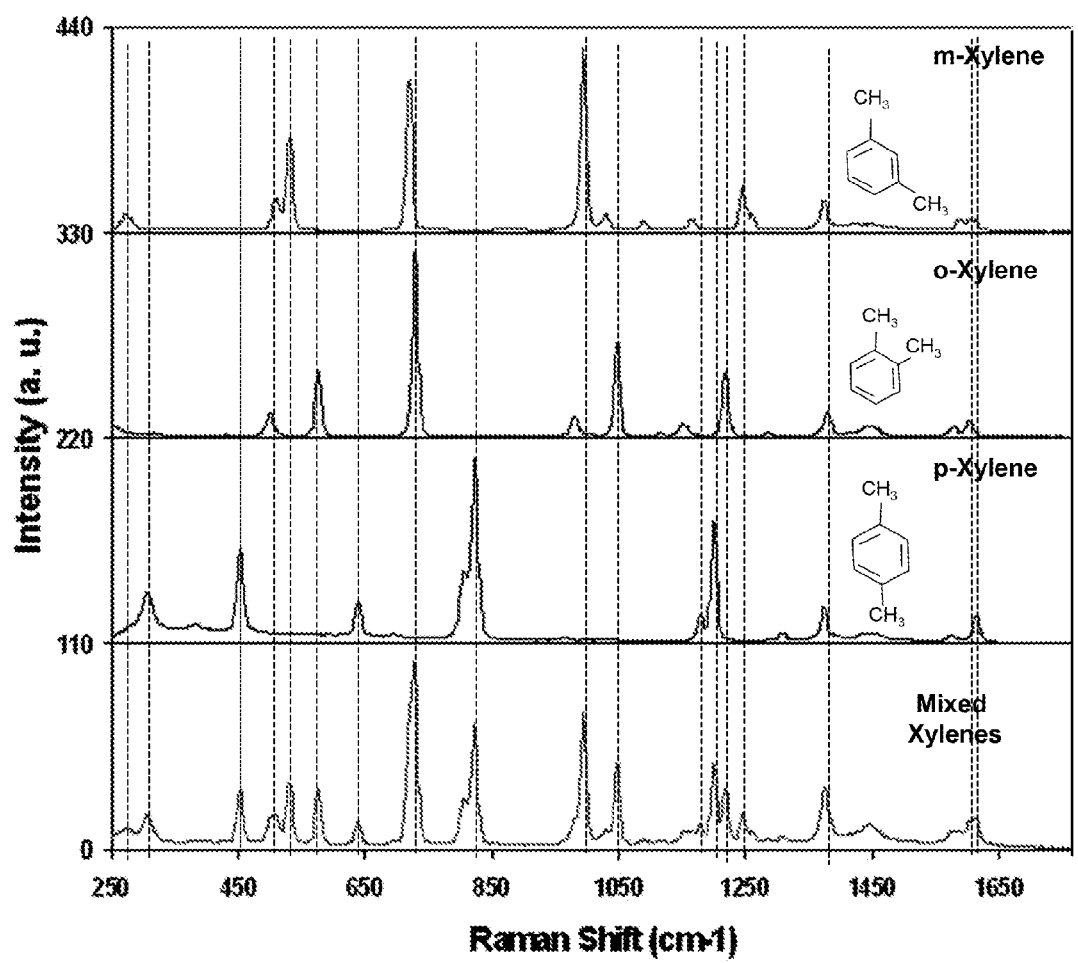

FIG. 23C shows Raman spectra of xylenes. In this example, Raman spectrum of m-xylene, o-xylene, p-Xylene, and mixed xylene are demonstrated separately. As shown in FIG. 23C, each chemical has its own chemical spectral fingerprint, even though the mass of those different xylenes are exact the same. On the other hand, Raman spectrum of mixed xylene shows little interference among those 3 different xylenes. Then, each chemical can be distinctively identified, therefore, Raman methods is one of the best chemical identification ways with spectral fingerprint capability.

Figure 25:
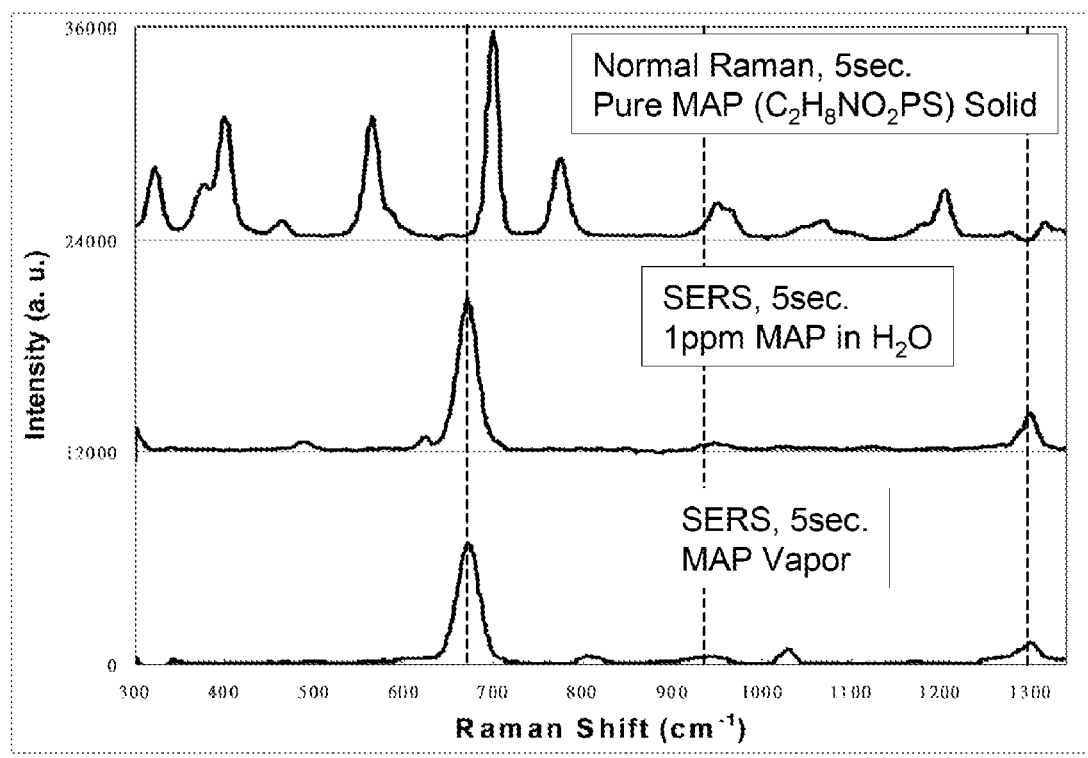
FIG. 25 shows a normal Raman spectrum and a SERS spectrum of methamidophos, a common pesticide and nerve agent stimulant.

Another experiment was carried out using methamidophos (MAP) which is a key pesticide; nerve agent stimulant. A trace amount of the chemical is introduced in liquid phase and vapor phase, respectively. The SERS spectra of these samples are compared against normal Raman spectrum of a pure MAP solid sample. As shown in FIG. 25, both liquid sample and vapor sample show MAP spectrum signature. It demonstrates that MAP vapor detection sensitivity is better than 40 parts per billion (ppb).

In the foregoing description and examples, limited and narrow interpretation of descriptive language intended to better illustrate the invention is not to be construed as limiting in any way nor to limit the scope of the invention contemplated by the inventor. It will be clear that the invention may be practiced otherwise than as particularly described in the foregoing description and examples. Numerous modifications and variations of the present invention are possible in light of the above teachings and, therefore, are within the scope of the appended claims.

The invention claimed is:

1. A sensing device for surface-enhanced Raman spectroscopy (SERS), comprising:
    a substrate;
    a plurality of nano structures over the substrate, wherein at least one of the nano structures comprises an active SERS nano surface; and
    an adsorption layer on the active SERS nano surface.

2. The sensing device of claim 1, wherein the nano structures are three dimensional objects each having a width between about 1 nm and about 300 nm.

3. The sensing device of claim 1, wherein the active SERS nano surface comprises a metallic material.

4. The sensing device of claim 1, wherein the plurality of nano structures include at least one or recesses, nano rods or nano holes.

5. The sensing device of claim 1, wherein adjacent nano structures have spacings between about 1 nm and about 1000 nm.

6. The sensing device of claim 1, wherein the nano structures have heights between about 1 nm and about 100 nm.

7. The sensing device of claim 1, wherein the one of the nano structures comprises an inactive SERS nano surface in proximity to the active nano SERS surface.

8. The sensing device of claim 1, wherein the adsorption layer comprises a material selected from a group consisting of $TiO_2$, $SiO_2$, $Al_2O_3$, $Si_3N_4$, $Ta_2O_5$, ZnO, Zr oxide, Hf oxide, Y oxide, Ag oxide, Au oxide, Sn oxide, Sb oxide, and a metal doped with chlorine or chloride.

9. The sensing device of claim 1, wherein the adsorption layer comprises a polymer selected from a group consisting of Ethylene Chlorotrifluoroethylene (ECTFE), Poly(ethylene-co-butyl acrylate-co-carbon monoxide) (PEBA), Poly (allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), and Polyvinylprorolidone (PVP).

10. The sensing device of claim 1, wherein the adsorption layer has a thickness between 0.5 nm and 500 nm.

11. A method for detecting a trace amount of a chemical substance, comprising:
   introducing a chemical substance to a nano structure over a substrate, wherein the chemical substance is provided in the form of a gas, a liquid, a powder, a gel, an aerosol, a solid, or a combination thereof, wherein the nano structure includes an active SERS nano surface and an adsorption layer at least partially disposed on the active SERS nano surface;
   allowing molecules of a chemical substance to adsorb on the adsorption layer;
   illuminating, by a laser beam, the nano structure and the molecules adsorbed on the adsorption layer;
   collecting light scattered by the molecules adsorbed on the adsorption layer on the nano structure; and
   analyzing a Raman spectrum of the scattered light to identify a composition of the chemical substance.

12. The method of claim 11, wherein the nano structure further comprises an inactive SERS nano surface in proximity to the active nano SERS surface.

13. The method of claim 11, wherein the nano structure further comprises a function layer on the substrate, wherein the nano structure is formed on the function layer.

14. The method of claim 11, further comprising applying an electric bias to the function layer to enhance molecular adsorption onto the adsorption layer during the step of illuminating.

15. The method of claim 11, further comprising applying a thermal bias to the adsorption layer to enhance molecular adsorption onto the adsorption layer during the step of illuminating.

16. The method of claim 13, wherein the function layer comprises a material selected from a group consisting of Ti, Ni, Cr, Pt, Ru, Ni—Cr alloy, NiCrN, Pt—Rh alloy, Cu—Au—Co alloy, Ir—Rh alloy and W—Re alloy.

17. The method of claim 13, wherein the function layer comprises a magnetic material.

18. The method of claim 17, further comprising applying a magnetic field to the active SERS nano surface.

19. A method of forming a surface-enhanced Raman spectroscopy (SERS) sensing device, comprising:
   forming a first layer over the substrate, wherein the first layer comprises an active material and wherein the substrate comprises an inactive material;
   forming a pattern on the first layer to define a plurality of nano structures; and
   selectively removing portions of the first layer using the pattern to produce nano structures each comprising a side wall, an active SERS nano surface, and an inactive SERS nano surface in proximity to the SERS active nano surface.

20. The method of claim 19, wherein the active material is selected from a group consisting of Ag, Au, Cu, Pt Al, Fe, Co, Ni, Ru, Rh, and Pd.

21. The method of claim 19, wherein the inactive material comprises an insulator.

22. The method of claim 19, wherein the inactive material is selected from a group consisting of silicon dioxide, aluminum oxide, silicon nitride, tantalum oxide, and titanium oxide.

23. The method of claim 19, wherein the active SERS nano surface has a width between about 1 nm and about 300 nm.

24. The method of claim 19, further comprising forming an adsorption layer on the first layer.

25. The method of claim 24, wherein the adsorption layer comprises a material selected from a group consisting of $TiO_2$, $SiO_2$, $Al_2O_3$, $Si_3N_4$, $Ta_2O_5$, ZnO, Zr oxide, Hf oxide, Y oxide, Ag oxide, Au oxide, Sn oxide, Sb oxide, and a metal doped with chlorine or chloride.

26. The method of claim 24, wherein the adsorption layer comprises a polymer selected from a group consisting of Ethylene, Chlorotrifluoroethylene (ECTFE), Poly(ethylene-co-butyl acrylate-co-carbon monoxide) (PEBA), Polytetrafluoroethylene (PTFE), Poly(allylamine hydrochloride) (PAH), Polystyrene sulfonate (PSS), Polyvinyl alcohol (PVA), Polyvinyl chloride (PVC), Polyvinyldene fluoride (PVDF), and Polyvinylprorolidone (PVP).

27. The method of claim 24, wherein the adsorption layer has a thickness between about 0.5 nm and about 500 nm.

28. The method of claim 19, further comprising forming an adhesion layer on the substrate, wherein the first layer is formed on the adhesion layer.

29. The method of claim 28, wherein the adhesion layer comprises Ni or Ti.

30. The method of claim 19, wherein the step of forming a pattern comprises:
   forming a mask layer on the first layer; and
   patterning the mask layer, wherein the step of selectively removing portions of the first layer comprises selecting removing a portion of the mask layer.

31. The method of claim 30, wherein the mask layer comprises a photoresist, an etch resistant material, an imprint polymer an anodizable metal.

32. The method of claim 30, wherein the step of forming a pattern comprises applying a photolithography process on the mask layer.

33. The method of claim 30, wherein the step of forming a pattern comprises applying an imprint process on the mask layer.

34. The method of claim 30, wherein the step of forming a pattern comprises anodizing the mask layer.

35. The method of claim 34, wherein the anodizable metal is Al.

36. The method of claim 30, wherein the step of selectively removing comprises etching at least a portion of the mask layer and a portion of the first layer.

37. The method of claim 19, wherein the nano structures have heights between about 1 nm and about 100 nm.

* * * * *